(12) United States Patent
Lee et al.

(10) Patent No.: US 10,860,053 B2
(45) Date of Patent: Dec. 8, 2020

(54) ULTRASOUND DIAGNOSIS APPARATUS AND METHOD OF CONTROLLING THE SAME

(71) Applicant: SAMSUNG MEDISON CO., LTD., Hongcheon-gun (KR)

(72) Inventors: Gi Tae Lee, Seongnam-si (KR); Yeon Ju Lee, Seongnam-si (KR); Dae Hwan Kim, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 79 days.

(21) Appl. No.: 16/179,065

(22) Filed: Nov. 2, 2018

(65) Prior Publication Data
US 2019/0155329 A1    May 23, 2019

(30) Foreign Application Priority Data

Nov. 17, 2017    (KR) .................. 10-2017-0153963

(51) Int. Cl.
*G06F 1/12*    (2006.01)
*A61B 8/00*    (2006.01)
(Continued)

(52) U.S. Cl.
CPC ................ *G06F 1/12* (2013.01); *A61B 8/565* (2013.01); *G06F 1/10* (2013.01); *H04L 67/42* (2013.01); *H04L 69/28* (2013.01); *H04N 5/76* (2013.01)

(58) Field of Classification Search
CPC ... G06F 1/12; G06F 1/10; A61B 8/565; H04L 67/42; H04L 69/28; H04N 5/76
See application file for complete search history.

(56) References Cited

U.S. PATENT DOCUMENTS 8,345,561 B2    1/2013    Edwards et al.
9,651,984 B2    5/2017    McGaughey
(Continued)

FOREIGN PATENT DOCUMENTS

JP    2004-220638 A    8/2004
JP    2016-015582 A    1/2016
KR    10-1580559 B1    12/2015

OTHER PUBLICATIONS

Communication dated Mar. 13, 2019, issued by the European Patent Office in counterpart European Application No. 18204823.1.

*Primary Examiner* — Dady Chery
(74) *Attorney, Agent, or Firm* — Sughrue Mion, PLLC

(57) ABSTRACT

Provided are an ultrasound diagnosis apparatus and method of controlling the same. The ultrasound diagnosis apparatus includes: a probe configured to acquire ultrasound image data with respect to an object by transmitting ultrasound signals to the object; a processor configured to obtain an ultrasound image based on the ultrasound image data, transmit the ultrasound image and a time stamp indicating a time point when the ultrasound image is obtained in real-time to a client apparatus, and store, in a memory, obtained ultrasound still cuts at respective first time intervals, together with the time stamp; and a communicator configured to receive a request for a still cut including a first time stamp from the client apparatus, wherein the processor is further configured to transmit to the client apparatus an ultrasound still cut corresponding to the first time stamp from among the stored obtained ultrasound still cuts.

19 Claims, 14 Drawing Sheets

(51) Int. Cl.
*G06F 1/10* (2006.01)
*H04L 29/06* (2006.01)
*H04N 5/76* (2006.01)

(56) References Cited

U.S. PATENT DOCUMENTS

| | | |
|---|---|---|
| 9,671,822 B2 | 6/2017 | Aweya |
| 2004/0146273 A1 | 7/2004 | Imanishi |
| 2013/0015975 A1* | 1/2013 | Huennekens ......... G06Q 50/22 |
| | | 340/573.1 |
| 2014/0171797 A1 | 6/2014 | Hershey et al. |
| 2015/0035959 A1* | 2/2015 | Amble .................. A61B 8/565 |
| | | 348/74 |
| 2017/0000462 A1 | 1/2017 | Washburn et al. |
| 2017/0078205 A1 | 3/2017 | Stalling et al. |
| 2017/0093757 A1 | 3/2017 | Gareau et al. |
| 2017/0169089 A1 | 6/2017 | Molnar |

* cited by examiner

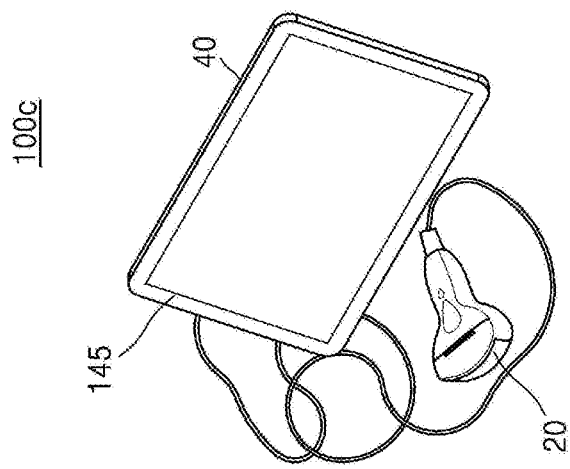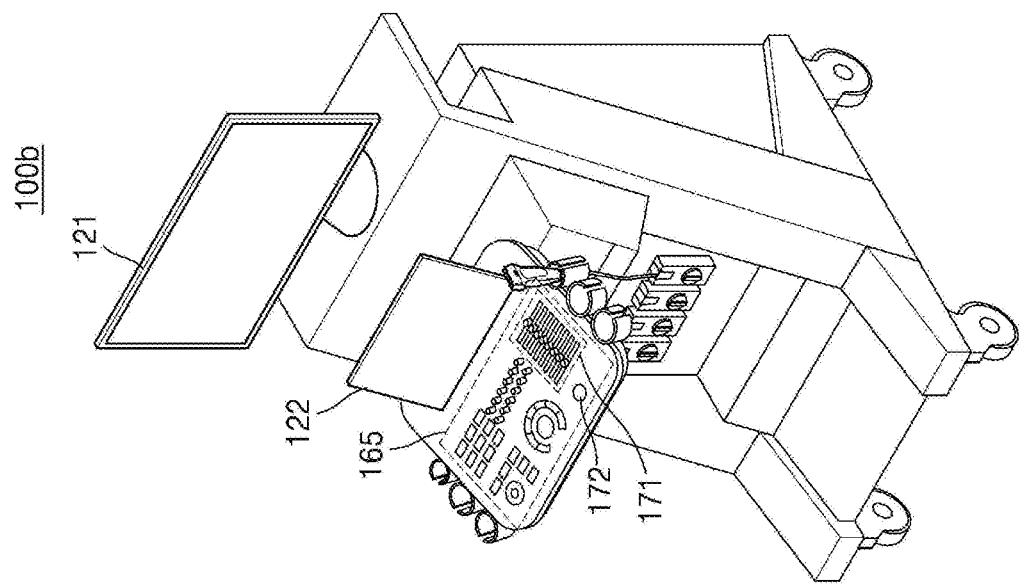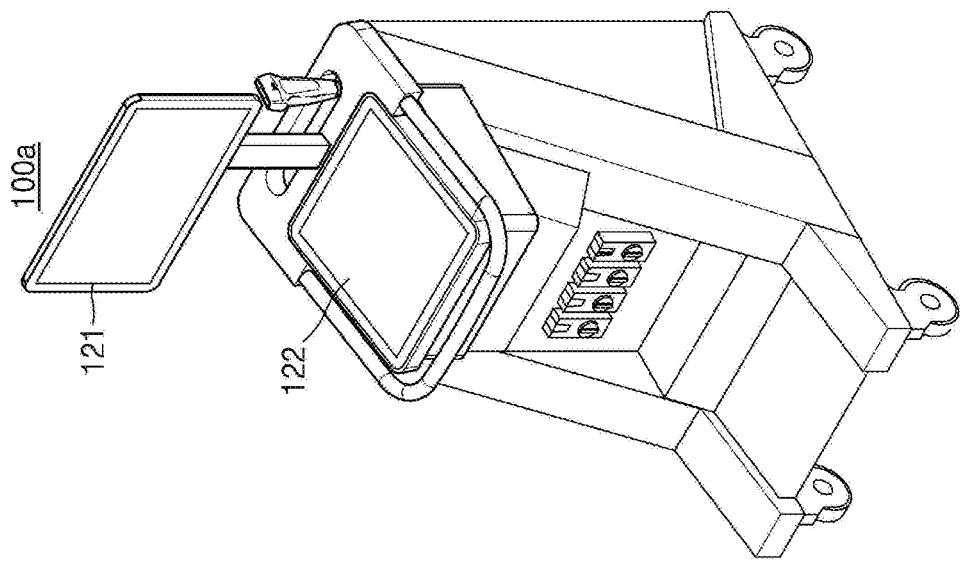

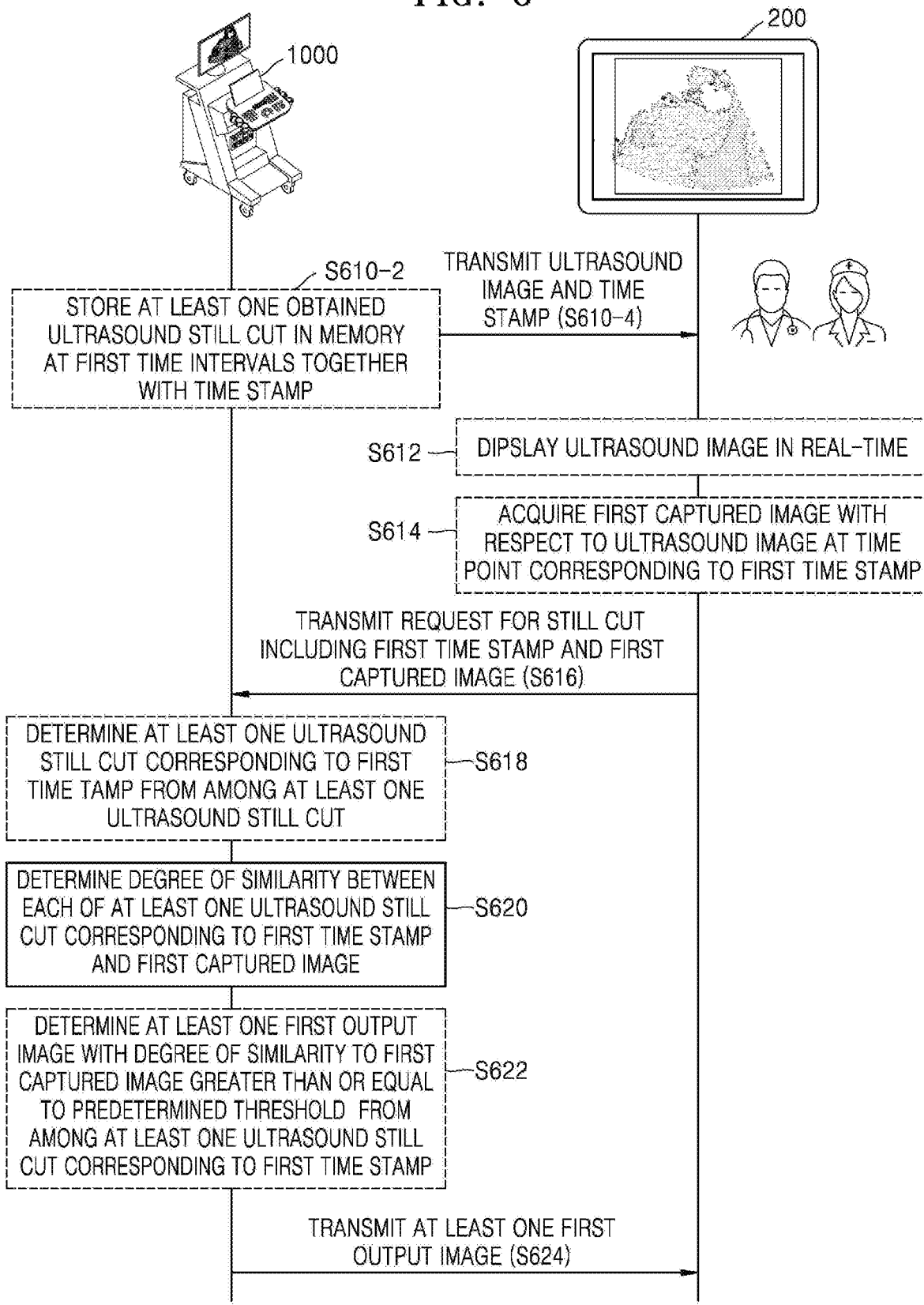

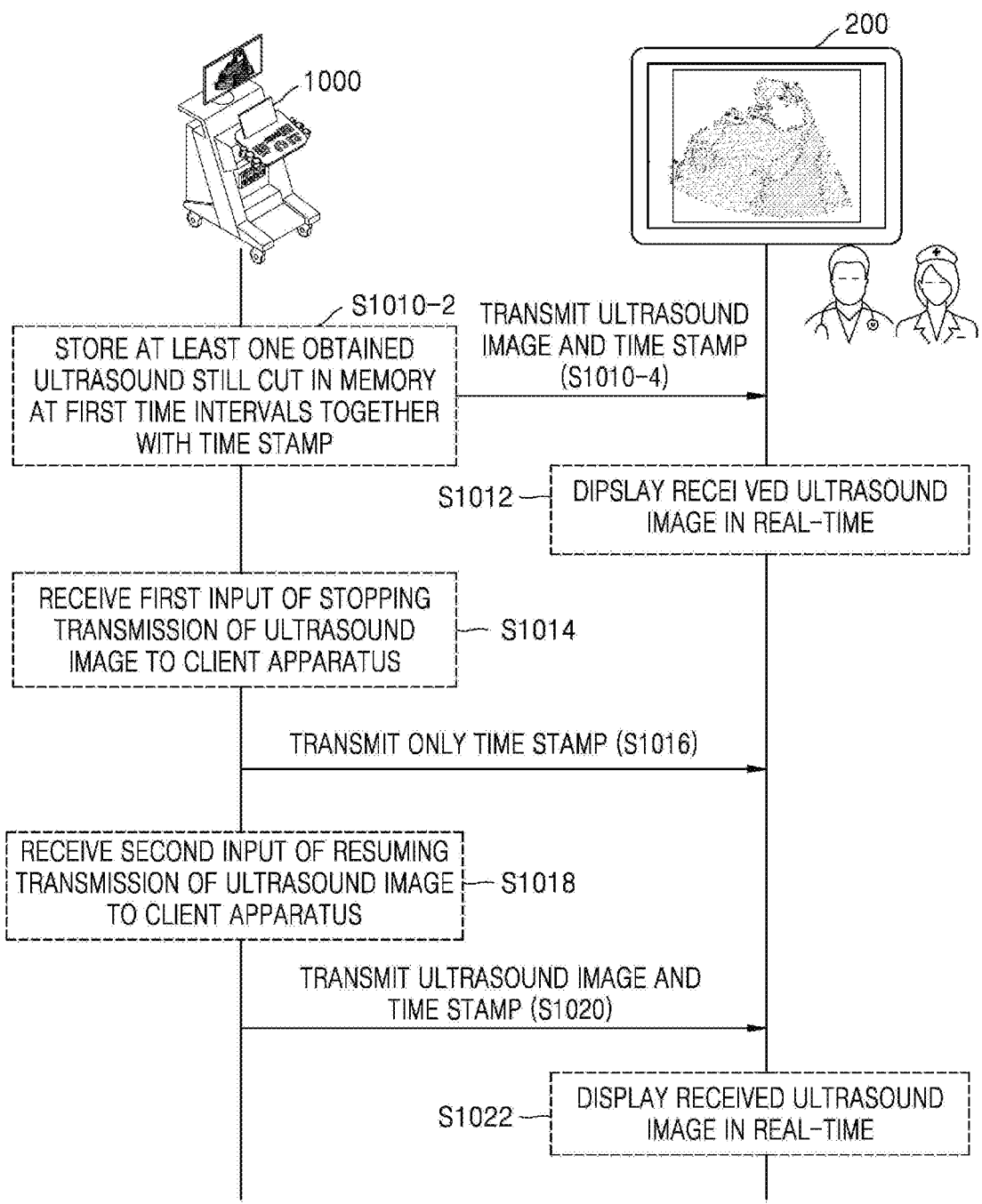

ULTRASOUND DIAGNOSIS APPARATUS AND METHOD OF CONTROLLING THE SAME

CROSS-REFERENCE TO RELATED APPLICATION(S)

This application is based on and claims priority under 35 U.S.C. § 119 to Korean Patent Application No. 10-2017-0153963, filed on Nov. 17, 2017, in the Korean Intellectual Property Office, the disclosure of which is incorporated by reference herein in its entirety.

BACKGROUND

1. Field

The disclosure relates to ultrasound diagnosis apparatuses, methods of controlling the same, and a computer program product including a computer-readable recording medium having recorded thereon a program for executing the methods on a computer.

2. Description of Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

A high level of expertise is required for operation of an ultrasound diagnostic apparatus for obtaining an ultrasound image and analysis of ultrasound images. Thus, a person who captures an ultrasound image is usually different from a person who interprets the captured ultrasound image. For example, a sonographer specializes in capturing an ultrasound image while a doctor diagnoses diseases in a patient based on the captured ultrasound image. However, since a person who captures an ultrasound image is different from a person who analyzes the captured ultrasound image, ultrasound images necessary for accurate diagnosis may, unintentionally, not be captured.

To solve this problem, a method whereby a person who remotely interprets an ultrasound image is able to monitor in real-time an ultrasound image simultaneously during ultrasound imaging has recently been introduced. For example, a doctor that is at a remote location may provide a guide to a sonographer while observing in real-time an ultrasound image being captured of a patient by the sonographer. According to the method, the doctor may request the sonographer (or an ultrasound diagnosis apparatus) to capture an ultrasound image corresponding to a moment, which is necessary for diagnosing a patient, while observing ultrasound images being transmitted in real-time.

However, the method may create, according to a network environment, a delay time required to transmit an ultrasound image captured by the sonographer to a device through which the doctor observes ultrasound images as well as a delay time required to transmit a doctor's guide to a device used by the sonographer.

Thus, when the doctor sends a request for a still cut that is an ultrasound image captured at a specific time point to the sonographer, the sonographer (or the ultrasound diagnosis apparatus) that is at a remote location may capture a still cut corresponding to a time point that occurs a delay time after the moment when the request is received. In other words, the sonographer may unintentionally capture a still cut corresponding to a time point different than the specific time point, i.e., a still cut other than a desired ultrasound image remotely observed by the doctor.

SUMMARY

Provided are ultrasound diagnosis apparatuses and methods of controlling the same, which are capable of providing, based on a time stamp representing a time point when an ultrasound diagnosis apparatus obtains an ultrasound image, a client apparatus with a still cut at a time point corresponding to a time point requested by the client apparatus.

Additional aspects will be set forth in part in the description which follows and, in part, will be apparent from the description, or may be learned by practice of the presented embodiments.

In accordance with an aspect of the disclosure, an ultrasound diagnosis apparatus includes: a probe configured to acquire ultrasound image data with respect to an object by transmitting ultrasound signals to the object; one or more processors configured to obtain an ultrasound image based on the ultrasound image data, transmit the ultrasound image and a time stamp indicating a time point when the ultrasound image is obtained in real-time to a client apparatus, and store, in a memory, at least one obtained ultrasound still cut at respective first time intervals, together with the time stamp; and a communicator configured to receive a request for a still cut including a first time stamp from the client apparatus, wherein the one or more processors are further configured to transmit to the client apparatus at least one ultrasound still cut corresponding to the first time stamp from among the stored at least one obtained ultrasound still cut.

In accordance with another aspect of the disclosure, a method of controlling an ultrasound diagnosis apparatus includes: acquiring ultrasound image data with respect to an object by transmitting ultrasound signals to the object; obtaining an ultrasound image based on the ultrasound image data; transmitting the ultrasound image and a time stamp indicating a time point when the ultrasound image is obtained in real-time to a client apparatus and storing, in a memory, at least one obtained ultrasound still cut at respective first time intervals, together with the time stamp; receiving a request for a still cut including a first time stamp from the client apparatus; and transmitting to the client apparatus at least one ultrasound still cut corresponding to the first time stamp from among the stored at least one obtained ultrasound still cut.

In accordance with another aspect of the disclosure, a computer program product includes a non-transitory computer-readable recording medium having recorded thereon a program for performing the method of controlling an ultrasound diagnosis apparatus on a computer.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 2A, 2B, and 2C are diagrams respectively illustrating an ultrasound diagnosis apparatus according to an embodiment;

FIG. 6 is a flowchart of a method, performed by an ultrasound diagnosis apparatus, of transmitting at least one output image to a client apparatus, according to an embodiment;

FIG. 10 is a flowchart of a method, performed by an ultrasound diagnosis apparatus, of transmitting an ultrasound image and a time stamp to a client apparatus, according to an embodiment;

DETAILED DESCRIPTION

Figure 1:
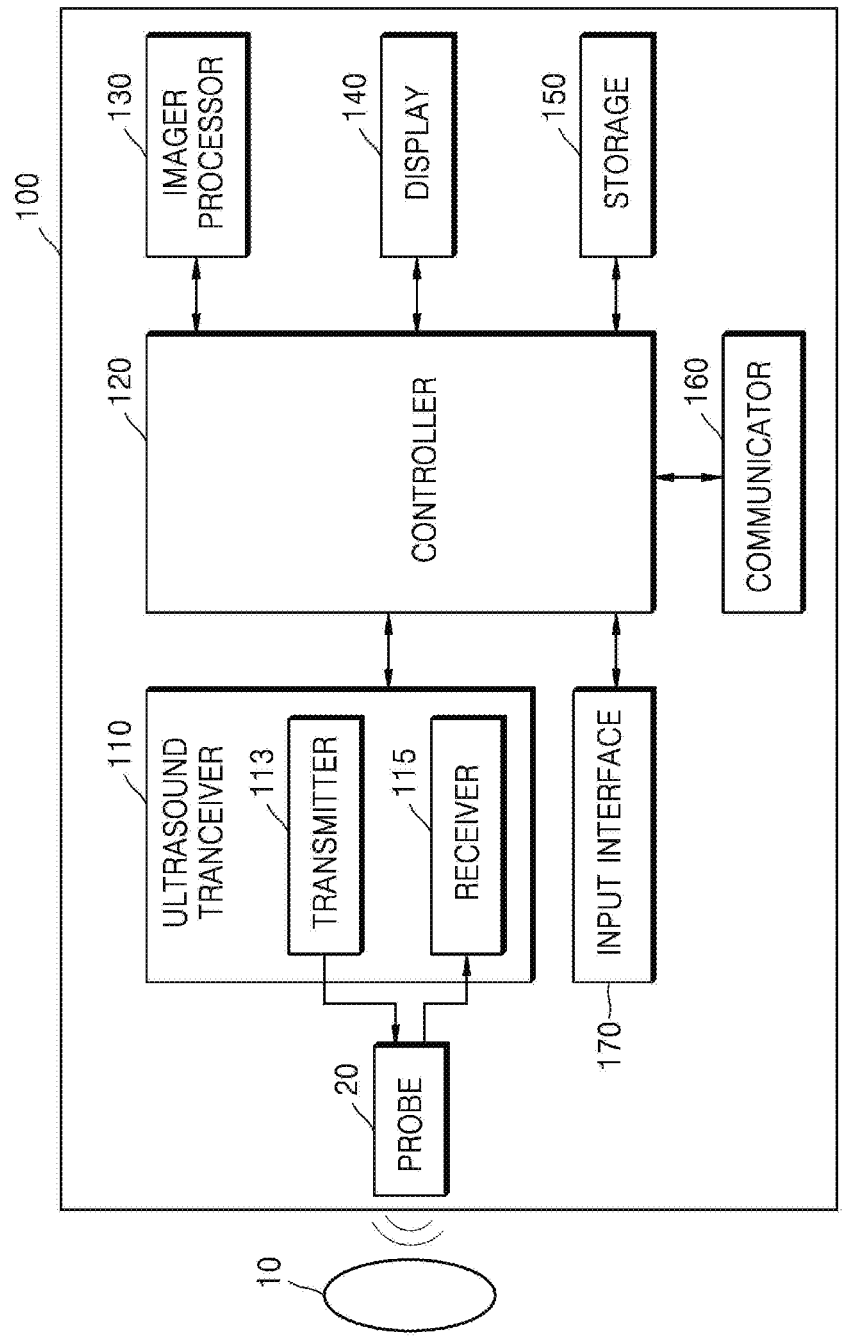
FIG. 1 is a block diagram illustrating an ultrasound diagnosis apparatus according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "module" or "unit" used herein may be implemented as software, hardware, firmware, or any combination of two or more thereof, and according to embodiments, a plurality of "modules" or "units" may be formed as a single element, or one "module" or "unit" may include a plurality of elements. Expressions such as "at least one of," when preceding a list of elements, modify the entire list of elements and do not modify the individual elements of the list.

Certain exemplary embodiments are described in greater detail below with reference to the accompanying drawings.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

In the present specification, examples of a client apparatus may include, but are not limited to, a smartphone, a tablet personal computer (PC), a PC, a smart television (TV), a mobile phone, a personal digital assistant (PDA), a laptop, a media player, an electronic book terminal, a digital broadcasting terminal, a navigation terminal, a kiosk, a digital camera, a home appliance, and other mobile or non-mobile computing devices. Furthermore, the client apparatus may be a wearable device such as a watch, glasses, a hair band, or a ring having a communication function and a data processing function. However, the client apparatus is not limited thereto, and may be any apparatus capable of receiving an ultrasound image from an ultrasound diagnosis apparatus and displaying the received ultrasound image.

Throughout the specification, an ultrasound image refers to an image of an object processed based on ultrasound signals transmitted to the object and reflected therefrom.

Hereinafter, embodiments of the present disclosure will be described in detail with reference to the accompanying drawings.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, a communicator 160, and an input interface 170.

The ultrasound diagnosis apparatus 100 may be of a cart-type or a portable-type ultrasound diagnosis apparatus, which is portable, movable, mobile, or hand-held. Examples of the ultrasound diagnosis apparatus 100 that is a portable-type ultrasound apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may transmit or receive control signals and data to or from the external apparatuses.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

FIGS. 2A, 2B, and 2C are diagrams illustrating ultrasound diagnosis apparatus according to an exemplary embodiment.

Referring to FIGS. 2A and 2B, the ultrasound diagnosis apparatus 100a and 100b may include a main display 121 and a sub-display 122. At least one of the main display 121 and the sub-display 122 may include a touch screen. The main display 121 and the sub-display 122 may display ultrasound images and/or various pieces of information processed by the ultrasound diagnosis apparatus 100a and 100b. The main display 121 and the sub-display 122 may provide graphical user interfaces (GUI), thereby receiving user's inputs of data to control the ultrasound diagnosis apparatus 100a and 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a and 100b may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may include a portable device. An example of the ultrasound diagnosis apparatus 100c implemented in a portable form as may include, for example, smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The main body 40 may include a touch screen 145. The touch screen 145 may display an ultrasound image, various pieces of information processed by the ultrasound diagnosis apparatus 100c, and a GUI.

Figure 3:
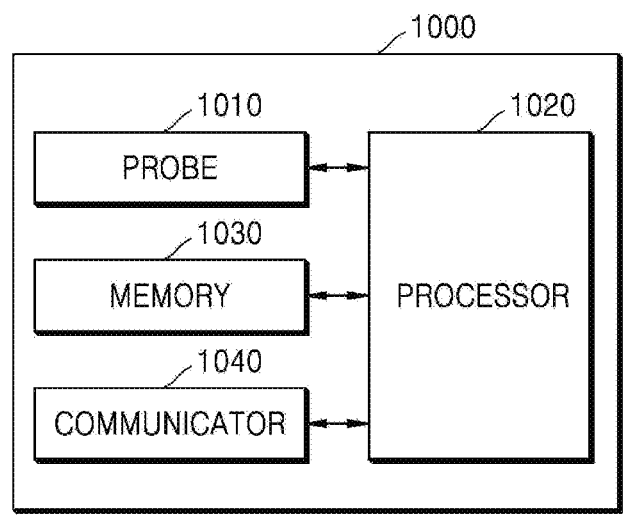
FIG. 3 is a block diagram of a configuration of an ultrasound diagnosis apparatus according to an embodiment.

FIG. 3 is a block diagram of an ultrasound diagnosis apparatus 1000 according to an embodiment.

According to an embodiment, the ultrasound diagnosis apparatus 1000 may include any image processing apparatus capable of obtaining an ultrasound image based on ultrasound image data acquired by performing an ultrasound scan. Furthermore, the ultrasound diagnosis apparatus 1000 may include a computing device capable of controlling acquisition of ultrasound image data during an ultrasound scan.

Referring to FIG. 3, the ultrasound diagnosis apparatus 1000 according to the embodiment may include a probe 1010, a processor 1020, a memory 1030, and a communicator 1040.

In detail, the ultrasound diagnosis apparatus 1000 may be included in the ultrasound diagnosis apparatus 100 described with reference to FIG. 1. In this case, the probe 1010, the memory 1030, and the communicator 1040 of the ultrasound diagnosis apparatus 1000 may respectively correspond to the probe 20, the storage 150, and the communicator 160 of the ultrasound diagnosis apparatus 100 of FIG. 1. The processor 1020 may correspond to one or a combination of the controller 120 and the image processor 130 described with reference to FIG. 1. Furthermore, according to an embodiment, the probe 1010 or the processor 1020 may further perform a function of the ultrasound transceiver 110 described with reference to FIG. 1.

Furthermore, the components of the ultrasound diagnosis apparatus 1000 are not limited to those shown in FIG. 3. According to an embodiment, the ultrasound diagnosis apparatus 1000 may include more components than those shown in FIG. 3.

The probe 1010 may include a plurality of transducers and transmit ultrasound signals to an object via the plurality of transducers. The probe 1010 may receive ultrasound echo signals reflected from the object via the plurality of transducers. The probe 1010 may acquire ultrasound image data with respect to the object based on the received ultrasound echo signals.

The processor 1020 may control all operations of the probe 1010, the memory 1030, and the communicator 1040. The processor 1020 may control all operations of the ultrasound diagnosis apparatus 1000 by executing a program stored in the memory 1030. Furthermore, the processor 1020 may include one or more processors.

The processor 1020 may generate an ultrasound image of an object based on ultrasound image data with respect to the object. For example, the processor 1020 may obtain an ultrasound image by processing in real-time ultrasound image data acquired by scanning the object via the probe 1010. The ultrasound image generated in real-time by the processor 1020 may be a still image or moving image. Furthermore, the processor 1020 may control a display (not shown) to display the generated ultrasound image.

According to an embodiment, the processor 1020 may transmit an ultrasound image and a time stamp indicating a time point when the ultrasound image is acquired in real-time to a client apparatus.

Furthermore, in the present specification, a time stamp may be a value or information indicating a time point when an ultrasound image is acquired after being processed. The time stamp may be a discontinuous value sampled at predetermined time intervals, or may be a continuous value. For example, when an ultrasound image is acquired at fifteen o'clock six minutes seventeen seconds, a time stamp indicating a time point when the ultrasound image is acquired may be a value '15:06:17'.

According to an embodiment, the processor 1020 may generate a separate file corresponding to a time stamp and transmit the separate file to a client apparatus together with an ultrasound image. According to another embodiment, the processor 1020 may record a time stamp on a part of a data structure including an ultrasound image and transmit the time stamp to a client apparatus together with the ultrasound image.

In an embodiment, when an ultrasound image acquired by the processor 1020 is a moving image, the processor 1020 may transmit the ultrasound image in such a manner that the ultrasound image is streamed to a client apparatus in real-time. Furthermore, in this case, the processor 1020 may transmit a continuous time stamp corresponding to the ultrasound image being streamed to the client apparatus.

A time stamp may be mapped to a frame in an ultrasound image corresponding to a given time point. According to an embodiment, a time stamp may be stored in a frame in an ultrasound image corresponding to a given time point. According to another embodiment, a time stamp file may contain information about its corresponding ultrasound image frame. In another embodiment, a look-up table indicating a correspondence relationship between a time stamp and a frame in an ultrasound image may be transmitted to a client apparatus, together with the time stamp and the ultrasound image.

Furthermore, according to an embodiment, the processor 1020 may process the acquired ultrasound image to thereby transmit the resulting ultrasound image in real-time to a client apparatus. For example, processing performed by the processor 1020 on the ultrasound image may include transcoding. The processor 1020 may perform the processing to convert the acquired ultrasound image into an ultrasound image with a lower resolution than an original image and transmit the resulting image to the client apparatus. In another embodiment, the processor 1020 may provide the acquired ultrasound image to an external server and obtain a processed ultrasound image from the external server. By performing processing, it is possible to reduce a size of an ultrasound image being transmitted to a client apparatus, thereby accommodating a limited network bandwidth. Since an ultrasound image generated by the ultrasound diagnosis apparatus 1000 has a high resolution, the ultrasound image may often not be transmitted to the client apparatus due to the limited network bandwidth. Thus, the ultrasound diagnosis apparatus 1000 may transcode the ultrasound image into a lower resolution ultrasound image to thereby transmit the resulting ultrasound image to the client apparatus.

According to an embodiment, the processor 1020 may control the memory 1030 to store at least one acquired ultrasound still cut at respective first time intervals, together with their corresponding time stamps. An ultrasound still cut corresponds to an ultrasound still image obtained from echo signals. For example, the processor 1020 may control the memory 1030 to store an ultrasound still cut with respect to an ultrasound image acquired in real-time every first time interval. Furthermore, the processor 1020 may control the memory 1030 to store a time stamp corresponding to an ultrasound still cut every first time interval, together with the ultrasound still cut. In this case, the ultrasound still cut may be an original version of an ultrasound image acquired by the processor 1020 based on ultrasound image data. An original image may have a higher resolution than a frame in an ultrasound image being streamed to a client apparatus. The original image may also have various file formats. However, embodiments are not limited thereto, and an ultrasound still cut may mean ultrasound image data or raw data from which the processor 1020 generates an ultrasound image.

In detail, the first time interval may be 0.1 second. For example, the processor 1020 may control the memory 1030 to store a first ultrasound still cut with respect to an ultrasound image acquired at 15 o'clock 6 minutes 17.2 seconds, together with a time stamp of '15:06:17:20'. In this case, the processor 1020 may control the memory 1030 to store, together with a time stamp of '15:06:17:30', a second ultrasound still cut with respect to an ultrasound image acquired at 15 o'clock 6 minutes 17.3 seconds as an ultrasound still cut that is continuous with respect to the first ultrasound still cut. In the same manner, the processor 1020 may control the memory 1030 to store, together with a time stamp of '15:06:17:40', a third ultrasound still cut with respect to an ultrasound image acquired at 15 o'clock 6 minutes 17.4 seconds as an ultrasound still cut that is continuous with respect to the second ultrasound still cut.

In an embodiment, the first time interval may be a preset value or a value determined by the processor 1020. For example, the processor 1020 may determine the first time interval based on a network delay time between the ultrasound diagnosis apparatus 1000 and a client apparatus. An operation of the processor 1020 determining the first time interval based on a network delay time will be described in more detail below with reference to FIG. 4.

According to an embodiment, the processor 1020 may receive a request for a still cut including a first time stamp from a client apparatus via the communicator 1040. For example, the client apparatus may be a device that receives an acquired ultrasound image from the ultrasound diagnosis apparatus 1000 at a remote location to stream the ultrasound image in real-time. Furthermore, while observing ultrasound images being streamed, a user of the client apparatus (e.g., a doctor) may enter a user's input into the client apparatus to request the ultrasound diagnosis apparatus 1000 for a still cut with respect to an ultrasound image being displayed at a current time point. The client apparatus may determine a first time stamp corresponding to an ultrasound image displayed at a time point when the user's input is received. Furthermore, the client apparatus may request a still cut including the first time stamp from the ultrasound diagnosis apparatus 1000.

Since an ultrasound still cut has a higher resolution than a moving image being streamed, its file size may be relatively large. According to an embodiment, the processor 1020 may determine a resolution of an ultrasound still cut based on at least one or a combination of a storage capacity of the memory 1030, a remaining capacity of the memory 1030, a processing speed of the processor 1020, and a user setting. Furthermore, in an embodiment, the processor 1020 may determine a first time interval at which an ultrasound still cut is generated, based on at least one or a combination of a storage capacity of the memory 1030, a remaining capacity of the memory 1030, a processing speed of the processor 1020, and a user setting.

According to an embodiment, a time stamp may be stored in a predetermined region within a file of an ultrasound still cut. In another embodiment, the time stamp may be stored in a look-up table format, and a look-up table may contain information about a file of an ultrasound still cut corresponding to each time stamp.

The processor 1020 may determine, according to a request made by the client apparatus for a still cut, at least one ultrasound still cut corresponding to a first time stamp from among at least one ultrasound still cut stored in the memory 1030. The processor 1020 may determine, based on time stamps stored in the memory 1030 together with at least one ultrasound still cut, at least one ultrasound still cut corresponding to the first time stamp from among the stored at least one ultrasound still cut.

In an embodiment, the processor 1020 may determine, from among at least one ultrasound still cut stored in the memory 1030, at least one ultrasound still cut including a time stamp corresponding to a time point closest to a first time stamp. In another embodiment, the processor 1020 may determine, from among the stored at least one ultrasound still cut, a predetermined number of ultrasound still cuts, each including a time stamp corresponding to a time point close to the first time stamp. An operation of the processor 1020 determining at least one ultrasound still cut including a time stamp corresponding to a time point closest to a first time stamp will be described in more detail below with reference to FIG. 5.

The processor 1020 may transmit the determined at least one ultrasound still cut corresponding to the first time stamp to the client apparatus. The processor 1020 may control the communicator 1040 to transmit the determined at least one ultrasound still cut corresponding to the first time stamp to the client apparatus.

The communicator 1040 may include at least one element capable of communicating with at least one of a client apparatus, an external server, and an external database. For example, the communicator 1040 may include at least one of a short-range communication module, a wired communication module, and a wireless communication module.

Examples of a short-range wireless communication module may include, but are not limited to, a Bluetooth communication module, a Bluetooth Low Energy (BLE) communication module, a Near Field Communication (NFC) unit, a Wireless LAN (WLAN) communication module, a ZigBee communication module, an Infrared Data Association (IrDA) communication module, a Wi-Fi Direct (WFD) communication module, an Ultra Wideband (UWB) communication module, and an Ant+ communication module.

The communicator 1040 may perform communication between the ultrasound diagnosis apparatus 1000 and a client apparatus based on control by the processor 1020. According to an embodiment, the communicator 1040 may transmit an acquired ultrasound image in real-time to the client apparatus. Furthermore, the communicator 1040 may receive a request for a still cut including a first time stamp from the client apparatus and transmit at least one ultrasound still cut corresponding to the first time stamp to the client apparatus.

According to embodiments, by transmitting an ultrasound still cut image based on a time stamp, the ultrasound diagnosis apparatus 1000 may provide an ultrasound still cut that is close to a still cut requested by a client apparatus despite the presence of a network delay time.

Figure 4:
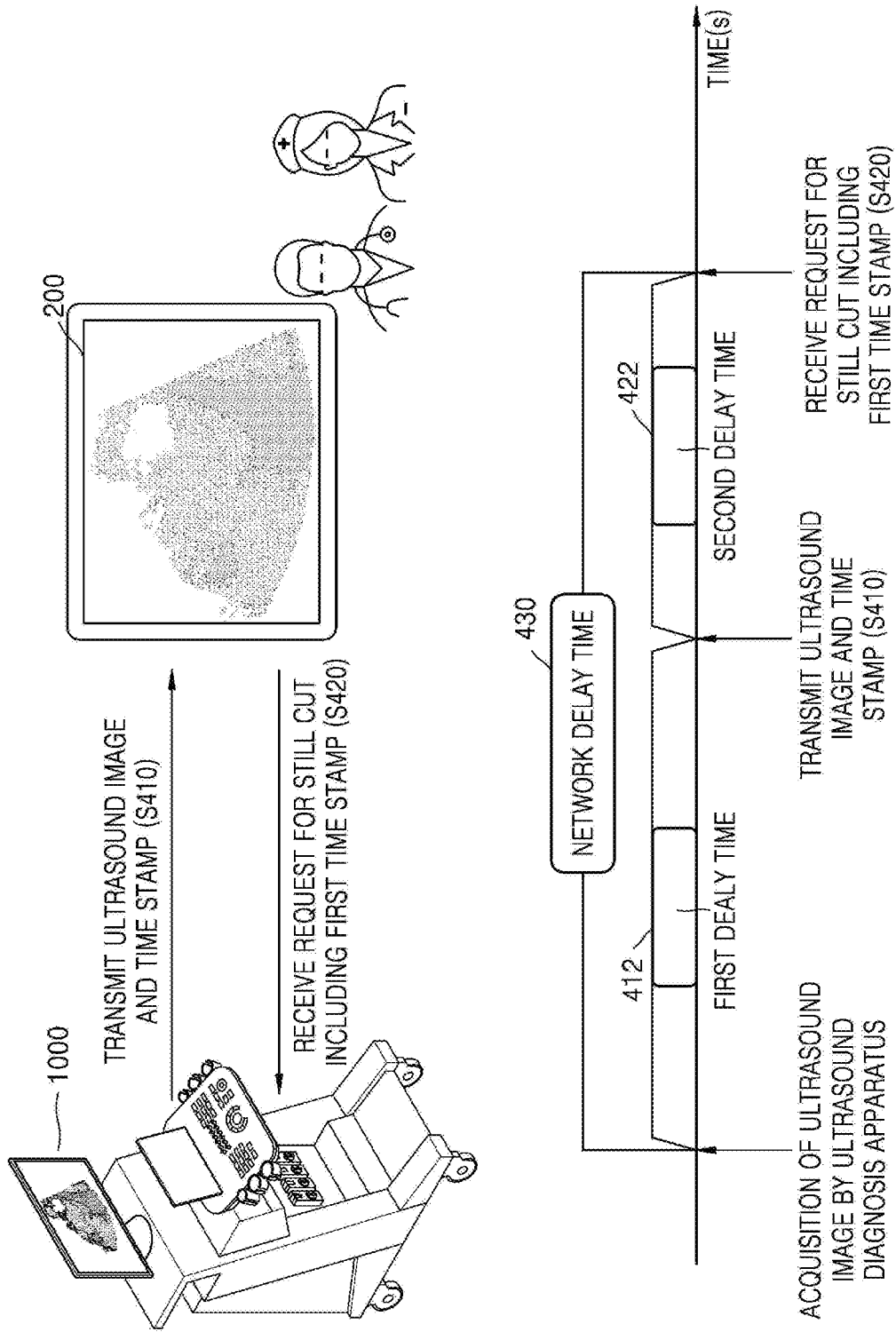
FIG. 4 is a diagram for explaining a network delay time between an ultrasound diagnosis apparatus and a client apparatus, according to an embodiment.

FIG. 4 is a diagram for explaining a network delay time between an ultrasound diagnosis apparatus 1000 and a client apparatus 200, according to an embodiment.

FIG. 4 shows one scenario for explaining a network delay time between the ultrasound diagnosis apparatus 1000 and the client apparatus 200, according to an embodiment.

When a time stamp is not used, a user of the client apparatus 200 sends a request for a still cut in an ultrasound image currently being displayed on a display of the client apparatus 200, the ultrasound diagnosis apparatus 1000 that is at a remote location obtains an ultrasound image at a time point when the request is received and transmits the ultrasound image to the client apparatus 200. A delay time required for the ultrasound diagnosis apparatus 1000 to transmit an ultrasound image to the client apparatus 200 as well as a delay time required for the ultrasound diagnosis apparatus 1000 to receive a request for a still cut from the client apparatus 200 occur during this operation. In this case, since there is a delay time between a time point when the ultrasound diagnosis apparatus 1000 acquires an ultrasound image and a time point when the client apparatus 200 receives the ultrasound image to display the same, the ultrasound diagnosis apparatus 1000 may not correctly determine which image is captured at a time point corresponding to an ultrasound image requested by the client apparatus 200. Furthermore, since a delay time varies according to a network environment, a processing time of the ultrasound diagnosis apparatus 1000, a processing time of the client apparatus 200, etc., it is difficult for the ultrasound diagnosis apparatus 1000 to precisely recognize information about the delay time. Thus, the user of the client apparatus 200 eventually receives an ultrasound image that is not the image requested via the client apparatus 200.

According to embodiments, to solve the above-described problem, by storing, in the memory 1030, ultrasound still cuts with respect to an ultrasound image at predetermined time intervals, the ultrasound diagnosis apparatus 1000 may provide an ultrasound still cut based on a time stamp according to a request made by the client apparatus 200 for a still cut including a time stamp.

The memory 1030 of the ultrasound diagnosis apparatus 1000 may have a limited capacity. In other words, the number of ultrasound still cuts that the memory 1030 is able to hold may be limited. Accordingly, the ultrasound diagnosis apparatus 1000 may determine a first time interval at which an ultrasound still cut is stored based on a network delay time 430 in order to transmit an ultrasound still cut corresponding to a request made by the client apparatus 200 for a still cut.

In this case, the network delay time 430 may include a first delay time 412 required for the ultrasound diagnosis apparatus 1000 to transmit an ultrasound image and a time stamp corresponding to the ultrasound image to the client apparatus 200 (S410) and a second delay time 422 required for the ultrasound diagnosis apparatus 1000 to receive a request for a still cut including a first time stamp from the client apparatus 200 (S420). The network delay time 430 may further include the time required for the ultrasound diagnosis apparatus 1000 to transcode an acquired ultrasound image to transmit the resulting ultrasound image to the client apparatus 200.

According to an embodiment, the ultrasound diagnosis apparatus 1000 may determine the network delay time 430. Furthermore, the ultrasound diagnosis apparatus 1000 may determine a first time interval based on the determined network delay time 430. For example, the ultrasound diagnosis apparatus 1000 may determine the first time interval by using Equation (1) below. However, embodiments are not limited thereto, and the ultrasound diagnosis apparatus 1000 may determine the first time interval according to various embodiments.

"first time interval (sec)=network delay time 430 (sec)×capacity per ultrasound still cut/allocated capacity of the memory 1030" (1)

According to an embodiment, by determining the first time interval based on the network delay time 430, the ultrasound diagnosis apparatus 1000 may store in the memory 1030 at least one ultrasound still cut acquired during a time between a current time point and a time point that is the network delay time 430 before the current time point.

Figure 5:
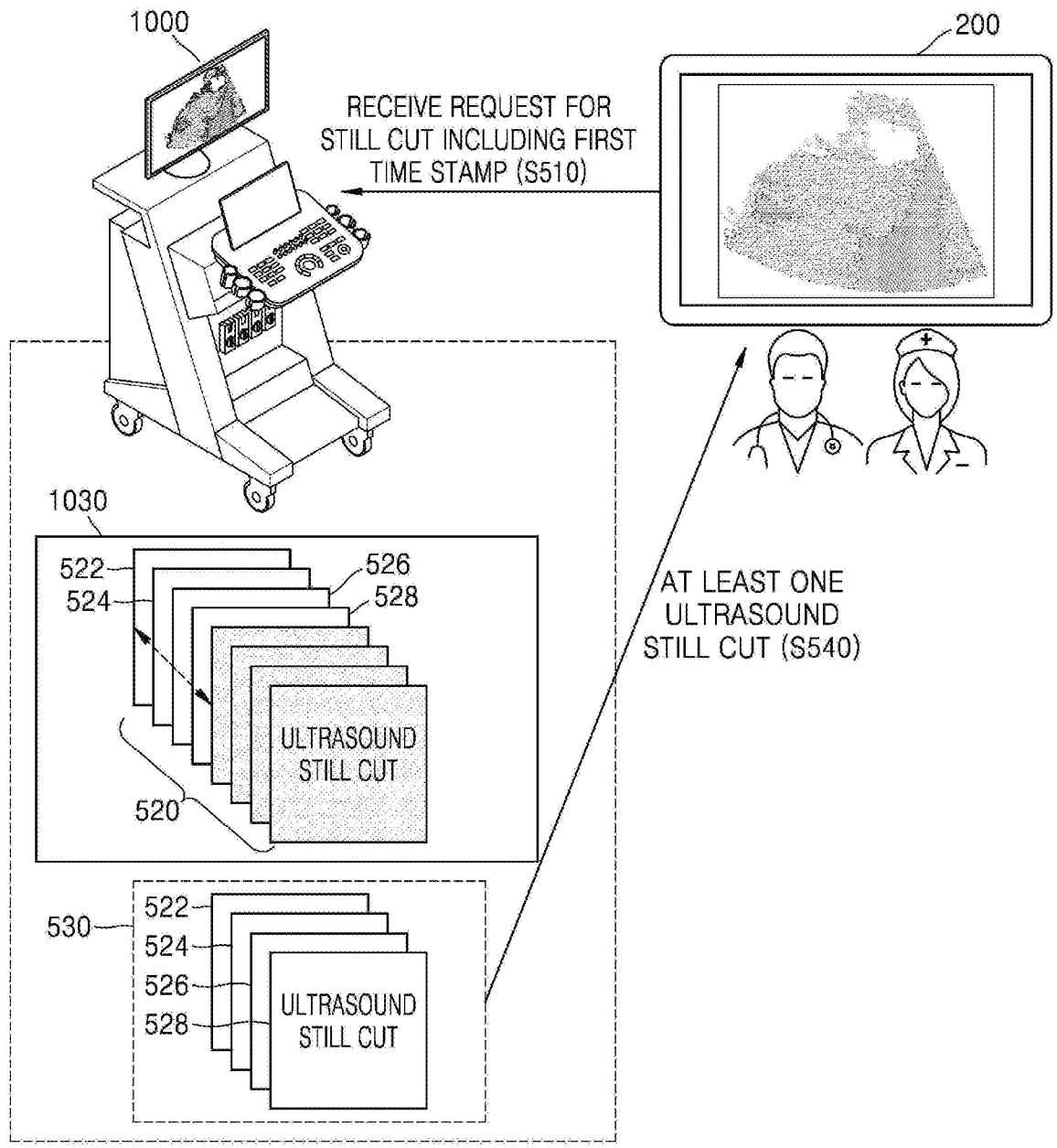
FIG. 5 is a diagram for explaining an operation of an ultrasound diagnosis apparatus transmitting at least one ultrasound still cut to a client apparatus, according to an embodiment.

FIG. 5 is a diagram for explaining an operation of an ultrasound diagnosis apparatus 1000 transmitting at least one ultrasound still cut to a client apparatus 200, according to an embodiment.

Referring to FIG. 5, the ultrasound diagnosis apparatus 1000 may receive a request for a still cut including a first time stamp from the client apparatus 200 (S510).

According to an embodiment, the ultrasound diagnosis apparatus 1000 may determine, based on the received request, determine at least one ultrasound still cut 530 corresponding to the first time stamp from among at least one ultrasound still cut 520 stored in the memory 1030 (S540).

Furthermore, in an embodiment, the at least one ultrasound still cut 520 may include an ultrasound still cut 1-1 522, an ultrasound still cut 1-2 524, an ultrasound still cut 1-3 526, and an ultrasound still cut 1-4 528. The ultrasound still cut 1-1 522 through the ultrasound still cut 1-4 528 may respectively include a time stamp 1-1 '15:16:17:40', a time stamp 1-2 '15:16:18:00', a time stamp 1-3 '15:16:18:20', and a time stamp 1-4 '15:16:18:40'. The first time stamp may be '15:16:18:30'.

According to an embodiment, the ultrasound diagnosis apparatus 1000 may determine at least one ultrasound still cut including a time stamp closest to the first time stamp '15:16:18:30' as at least one ultrasound still cut corresponding to the first time stamp '15:16:18:30'. The at least one ultrasound still cut including a time stamp closest to the first time stamp '15:16:18:30' may be the ultrasound still cut 1-3 526 and ultrasound still cut 1-4 528 respectively including the time stamp 1-3 '15:16:18:20' and time stamp 1-4 '15:16:18:40'. Thus, the ultrasound diagnosis apparatus 1000 may determine the ultrasound still cut 1-3 526 and ultrasound still cut 1-4 528 as the at least one ultrasound still cut corresponding to the first time stamp.

According to another embodiment, the ultrasound diagnosis apparatus 1000 may determine a predetermined number (e.g., four) of ultrasound still cuts, each including a time stamp closest to the first time stamp '15:16:18:30', as at least one ultrasound still cut corresponding to the first time stamp '15:16:18:30'. Referring to FIG. 5, four ultrasound still cuts respectively including time stamps closest to the first time stamp '15:16:18:30' may be the ultrasound still cut 1-1 522 through the ultrasound still cut 1-4 528 respectively including the time stamp 1-1 '15:16:17:40', time stamp 1-2 '15:16:18:00', time stamp 1-3 '15:16:18:20', and time stamp 1-4 '15:16:18:40'. Accordingly, the ultrasound diagnosis apparatus 1000 may determine the ultrasound still cut 1-1 522 through the ultrasound still cut 1-4 528 as the at least one ultrasound still cut 530 corresponding to the first time stamp '15:16:18:30'.

According to another embodiment, the ultrasound diagnosis apparatus 1000 may determine at least one ultrasound still cut, each including a time stamp that is within a predetermined time interval (e.g., 0.1 second) from the first time stamp '15:16:18:30', as at least one ultrasound still cut corresponding to the first time stamp '15:16:18:30'. The at least one ultrasound image including a time stamp that is within a time interval of 0.1 second from the first time stamp '15:16:18:30' may be the ultrasound still cut 1-3 526 and ultrasound still cut 1-4 528 respectively including the time stamp 1-3 '15:16:18:20' and time stamp 1-4 '15:16:18:40'. Thus, the ultrasound diagnosis apparatus 1000 may determine the ultrasound still cut 1-3 526 and ultrasound still cut 1-4 528 as the at least one ultrasound still cut corresponding to the first time stamp.

However, a method whereby the ultrasound diagnosis apparatus 1000 determines at least one ultrasound still cut corresponding to the first time stamp is not limited to the above-described embodiments, and the ultrasound diagnosis apparatus 1000 may determine at least one ultrasound still cut corresponding to the first time stamp based on various methods.

FIG. 6 is a flowchart of a method, performed by an ultrasound diagnosis apparatus 1000, of transmitting at least one output image to a client apparatus 200, according to an embodiment.

In detail, FIG. 6 shows an example in which the ultrasound diagnosis apparatus 1000 provides the client apparatus 200 with an ultrasound still cut that is more similar to a still cut requested by the client apparatus 200, according to an embodiment.

The ultrasound diagnosis apparatus 1000 may store at least one obtained ultrasound still cut in the memory (1030 of FIG. 3) at respective first time intervals, together with their corresponding time stamps (S610-2).

In an embodiment, the ultrasound diagnosis apparatus 1000 may obtain an ultrasound image by processing in real-time ultrasound image data acquired by scanning an object via the probe (1010 of FIG. 3). Furthermore, the ultrasound diagnosis apparatus 1000 may store an ultrasound still cut with respect to an ultrasound image obtained in real-time every first time interval, together with its corresponding time stamp.

The ultrasound diagnosis apparatus 1000 may transmit an obtained ultrasound image and a time stamp indicating a time when the ultrasound image is obtained to the client apparatus 200 (S610-4). Furthermore, operation S610-4 may be performed simultaneously with operation S610-2.

In an embodiment, the ultrasound diagnosis apparatus 1000 may transmit an obtained ultrasound image and a time stamp in real-time to the client apparatus 200. The ultrasound diagnosis apparatus 1000 may perform predetermined processing on the obtained ultrasound image to increase a transmission speed. Furthermore, the ultrasound diagnosis apparatus 1000 may transmit the processed ultrasound image and the time stamp in real-time to the client apparatus 200. The processed ultrasound image may be an ultrasound image acquired by converting the obtained ultrasound image into an image with a lower resolution than an original image.

According to an embodiment, when the obtained ultrasound image is a moving image, the ultrasound diagnosis apparatus 1000 may transmit the ultrasound image in such a manner that the ultrasound image is streamed to the client apparatus 200 in real-time. Furthermore, in this case, the ultrasound diagnosis apparatus 1000 may transmit to the client apparatus 200 a continuous time stamp corresponding to the ultrasound image being streamed.

The client apparatus 200 may display the ultrasound image received from the ultrasound diagnosis apparatus 1000 on a display in real-time (S612).

In an embodiment, the client apparatus 200 may display in real-time the ultrasound image and its corresponding time stamp received from the ultrasound diagnosis apparatus 1000. However, embodiments are not limited thereto, and the client apparatus 200 may display only an ultrasound image among the received ultrasound image and time stamp.

The client apparatus 200 may acquire a first captured image with respect to an ultrasound image displayed at a time point corresponding to a first time stamp (S614).

In an embodiment, the client apparatus 200 may receive from a user a capture input with respect to an ultrasound image displayed at a particular time point on a display of the client apparatus 200. For example, when the user of the client apparatus 200 observes ultrasound images being displayed and finds that an ultrasound image necessary for diagnosis of an object is displayed, the user may enter a capture input to control the client apparatus 200 to capture the ultrasound image being displayed at a current time point. The client apparatus 200 may acquire, based on the capture input, a first captured image by capturing the ultrasound image displayed at a time point when the captured input is received.

The client apparatus 200 may transmit the first captured image and a request for a still cut including the first time stamp to the ultrasound diagnosis apparatus 1000 (S616).

According to an embodiment, the first time stamp may include a value corresponding to the time point when the client apparatus 200 acquires the first captured image. Furthermore, the request for a still cut including the first time stamp may be a request for an image corresponding to the first captured image.

The ultrasound diagnosis apparatus 1000 may determine at least one ultrasound still cut corresponding to the first time stamp from among at least one ultrasound still cut stored in the memory 1030 (S618).

The embodiments described with reference to FIG. 5 may be applied to an operation of the ultrasound diagnosis apparatus 1000 determining at least one ultrasound still cut corresponding to the first time stamp. Thus, the same descriptions as are already provided with respect to FIG. 5 will be omitted herein.

The ultrasound diagnosis apparatus 1000 may determine the degree of similarity between each of the at least one ultrasound still cut corresponding to the first time stamp and the first captured image (S620).

According to an embodiment, the ultrasound diagnosis apparatus 1000 may determine the degree of similarity between each of the at least one ultrasound still cut corresponding to the first time stamp and the first captured image, which is used to quantify the degree of matching therebetween. Various known algorithms may be used to determine the degree of similarity between each of the at least one ultrasound still cut corresponding to the first time stamp and the first captured image. Examples of algorithms for determining the degree of similarity between images may include histogram comparing, template matching, and feature matching.

The ultrasound diagnosis apparatus 1000 may determine, based on the determined degree of similarity, at least one first output image from among the at least one ultrasound still cut corresponding to the first time stamp (S622).

In an embodiment, the ultrasound diagnosis apparatus 1000 may determine, from among the at least one ultrasound still cut corresponding to the first time stamp, at least one first output image with the degree of similarity to the first captured image that is greater than or equal to a predetermined threshold. In another embodiment, the ultrasound diagnosis apparatus 1000 may determine at least one first output image with a highest degree of similarity to the first captured image, from among the at least one ultrasound still cut corresponding to the first time stamp. An operation of the ultrasound diagnosis apparatus 1000 determining at least one first output image will be described in more detail below with reference to FIGS. 7A and 7B.

The ultrasound diagnosis apparatus 1000 may transmit the at least one first output image to the client apparatus 200 (S624). The at least one first output image may be an image corresponding to the first captured image.

According to embodiments, by determining a first output image based on a first time stamp and a first captured image received from the client apparatus 200, the ultrasound diagnosis apparatus 1000 may provide the client apparatus 200 with an ultrasound still cut that is relatively close to that requested by the client apparatus 200.

Figure 7A:
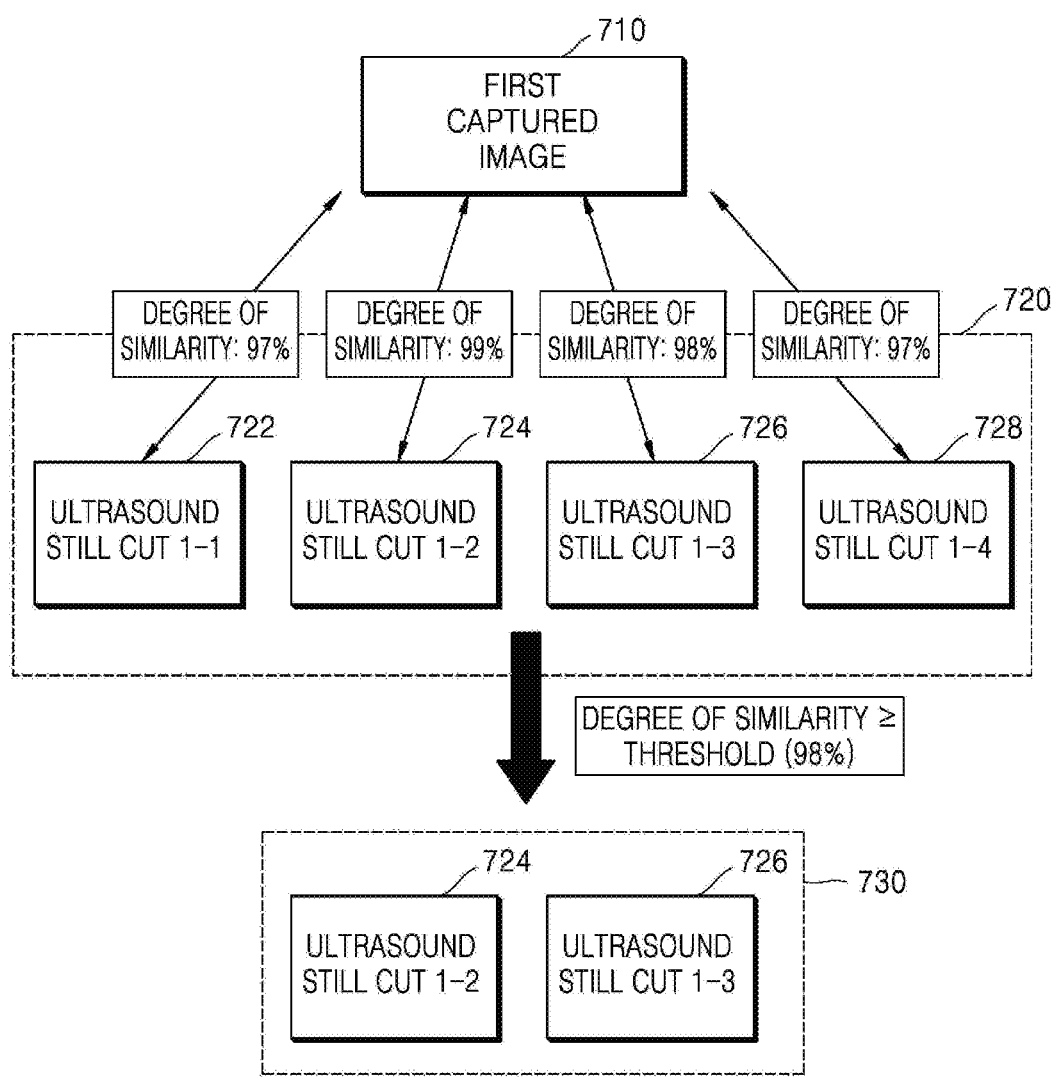
FIGS. 7A and 7B are diagrams for explaining an operation of an ultrasound diagnosis apparatus determining at least one output image, according to an embodiment.
Figure 7B:
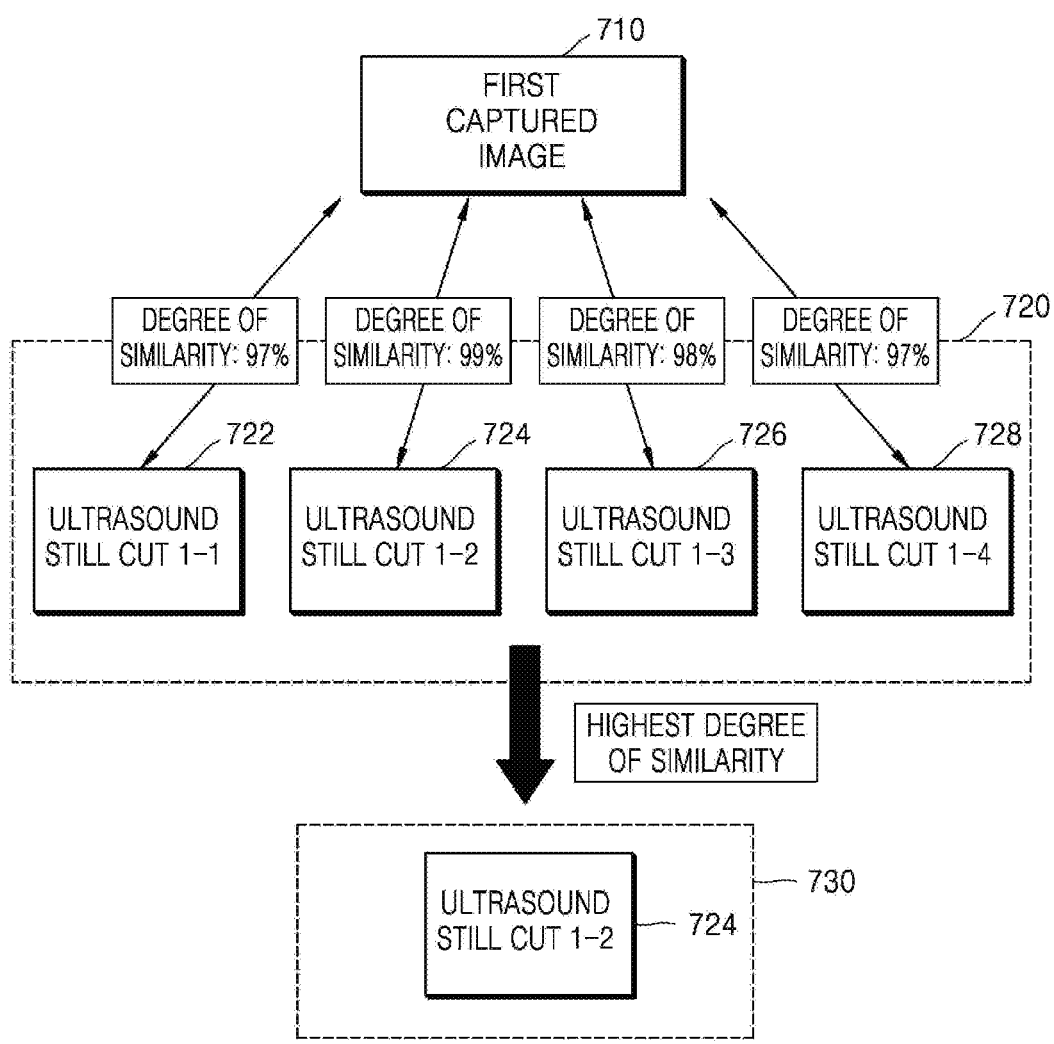

FIGS. 7A and 7B are diagrams for explaining an operation of the ultrasound diagnosis apparatus (1000 of FIG. 6) determining at least one output image, according to an embodiment.

In detail, FIG. 7A illustrates an example in which the ultrasound diagnosis apparatus 1000 determines at least one first output image 730 based on the degree of similarity between at least one ultrasound still cut 720 corresponding to a first time stamp and a first captured image 710.

According to an embodiment, the at least one ultrasound still cut corresponding to the first time stamp may include an ultrasound still cut 1-1 722, an ultrasound still cut 1-2 724, an ultrasound still cut 1-3 726, and an ultrasound still cut 1-4 728.

Furthermore, the ultrasound diagnosis apparatus 1000 may determine the degree of similarity between the first captured image 710 and each of the ultrasound still cut 1-1 722 through the ultrasound still cut 1-4 728 included in the at least one ultrasound still cut corresponding to the first time stamp. For example, the ultrasound still cut 1-1 722, the ultrasound still cut 1-2 724, the ultrasound still cut 1-3 726, and the ultrasound still cut 1-4 728 may respectively be determined to have the degrees of similarity of 97%, 99%, 98%, and 97% with respect to the first captured image 710.

In an embodiment, the ultrasound diagnosis apparatus 1000 may determine, from among the at least one ultrasound still cut 720 corresponding to the first time stamp, an ultrasound still cut with a degree of similarity to the first captured image 710 that is greater than or equal to a predetermined threshold (e.g., 98%) as the at least one first output image 730. In this case, the ultrasound diagnosis apparatus 1000 may determine the ultrasound still cut 1-2 724 and the ultrasound still cut 1-3 726 with the degrees of similarity to the first captured image 710, which are greater than or equal to 98%, as the at least one first output image 730.

In another embodiment, referring to FIG. 7B, the ultrasound diagnosis apparatus 1000 may determine, from among the at least one ultrasound still cut 720 corresponding to the first time stamp, an ultrasound still cut having a highest degree of similarity with respect to the first captured image 710 as the at least one first output image 730. In this case, the ultrasound diagnosis apparatus 1000 may determine, from among the at least one ultrasound still cut 720 corresponding to the first time stamp, the ultrasound still cut 1-2 724 having the highest degree of similarity with respect to the first captured image 710 as the at least one first output image 730.

Figure 8:
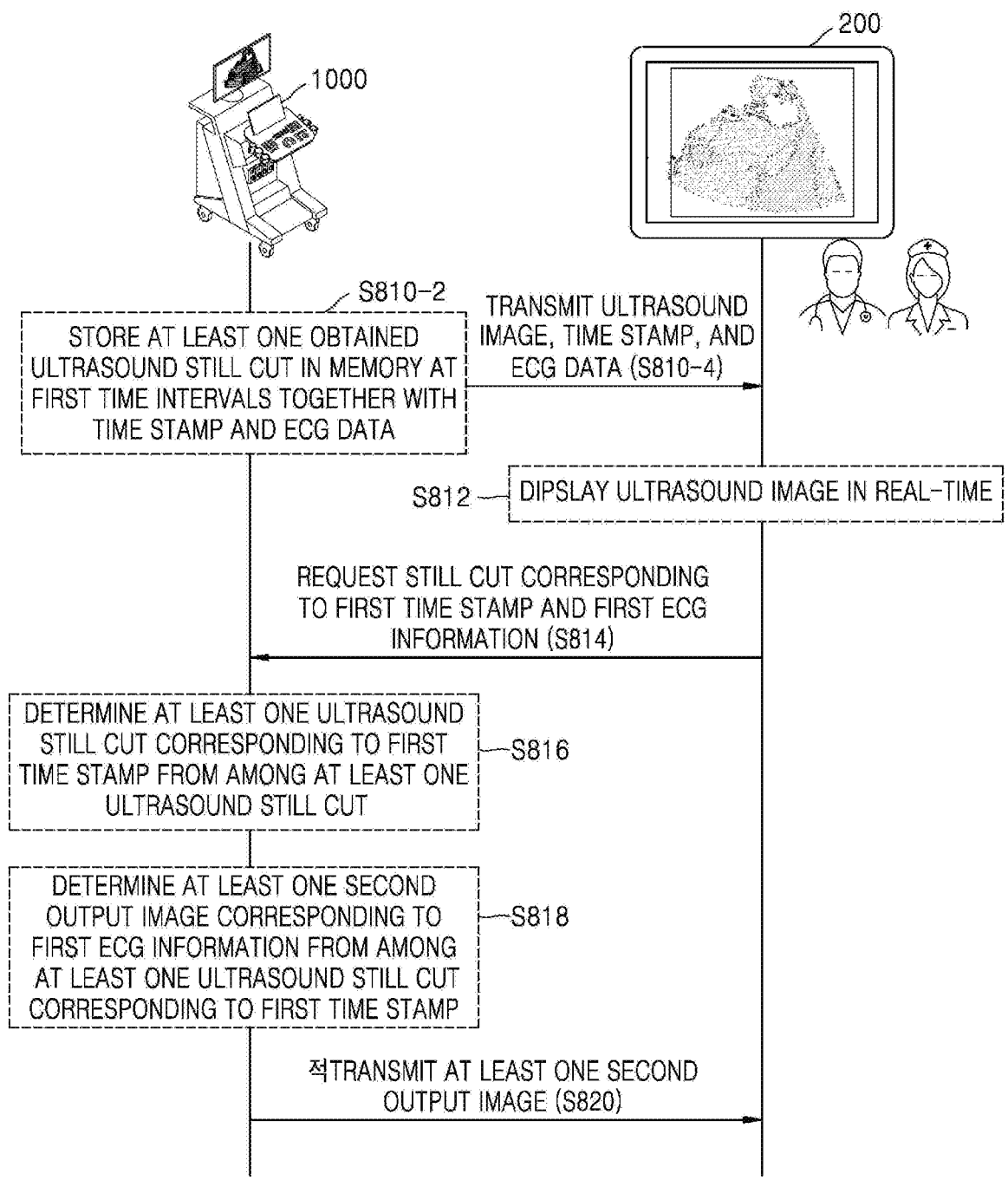
FIG. 8 is a flowchart of a method, performed by an ultrasound diagnosis apparatus, of transmitting at least one output image to a client apparatus based on a time stamp and electrocardiogram (ECG) data, according to an embodiment.

FIG. 8 is a flowchart of a method, performed by an ultrasound diagnosis apparatus 1000, of transmitting at least one output image to a client apparatus 200 based on a time stamp and electrocardiogram (ECG) data, according to an embodiment.

In detail, FIG. 8 shows another example in which the ultrasound diagnosis apparatus 1000 provides the client apparatus 200 with an ultrasound still cut that is more similar to a still cut requested by the client apparatus 200, according to an embodiment.

The ultrasound diagnosis apparatus 1000 may store at least one obtained ultrasound still cut in the memory (1030 of FIG. 3) at respective first time intervals, together with their corresponding time stamps and ECG data (S810-2).

In an embodiment, the ultrasound diagnosis apparatus 1000 may obtain an ultrasound image and ECG data with respect to an object. According to an embodiment, the ultrasound diagnosis apparatus 1000 may include an ECG measuring unit (not shown) for acquiring ECG data. In another embodiment, the ultrasound diagnosis apparatus 1000 may receive ECG data acquired in real-time from an external ECG measuring device. Furthermore, the ultrasound diagnosis apparatus 1000 may store, in the memory 1030, an ultrasound still cut with respect to an ultrasound image every first time interval, together with its corresponding time stamp and ECG data.

The ultrasound diagnosis apparatus 1000 may transmit an obtained ultrasound image, a time stamp, and ECG data to the client apparatus 200 (S810-4). Furthermore, operation S810-4 may be performed simultaneously with operation S810-2. The embodiments described with respect to operation S610-4 in FIG. 6 may be applied to the operation (S810-4) of the ultrasound diagnosis apparatus 1000 transmitting the obtained ultrasound image, time stamp, and ECG data to the client apparatus 200.

The client apparatus 200 may display the ultrasound image received from the ultrasound diagnosis apparatus 1000 on a display in real-time (S812).

In an embodiment, the client apparatus 200 may display in real-time the ultrasound image, its corresponding time stamp, and ECG data received from the ultrasound diagnosis apparatus 1000. However, embodiments are not limited thereto, and the client apparatus 200 may display only the received ultrasound image or at least one of the received ultrasound image, time stamp, and ECG data.

The client apparatus 200 may request the ultrasound diagnosis apparatus 1000 for a still cut with respect to an ultrasound image corresponding to a first time stamp and first ECG information (S814).

For example, a user of the client apparatus 200 may observe ultrasound images being displayed via the display of the client apparatus 200 and detect an ultrasound image necessary for diagnosis of the object. In this case, the user may enter a user's input into the client apparatus 200 to request the ultrasound diagnosis apparatus 1000 for a still cut with respect to an ultrasound image being displayed at a current time point. The client apparatus 200 may determine a first time stamp and first ECG information corresponding to an ultrasound image displayed at a time point when the user's input is received. Furthermore, the client apparatus 200 may request the ultrasound diagnosis apparatus 1000 for a still cut corresponding to the first time stamp and the first ECG information.

The ultrasound diagnosis apparatus 1000 may determine at least one ultrasound still cut corresponding to the first time stamp from among the at least one ultrasound still cut stored in the memory 1030 (S816).

The embodiments described with respect to FIG. 5 may be applied to the operation of the ultrasound diagnosis apparatus 1000 determining at least one ultrasound still cut corresponding to the first time stamp. Thus, the same descriptions as are already provided with respect to FIG. 5 will be omitted herein.

The ultrasound diagnosis apparatus 1000 may determine at least one second output image corresponding to the first ECG information, from among the at least one ultrasound still cut corresponding to the first time stamp (S818).

In an embodiment, the ultrasound diagnosis apparatus 1000 may compare ECG information regarding each of the at least one ultrasound still cut corresponding to the first time stamp with the first ECG information. Furthermore, the ultrasound diagnosis apparatus 1000 may determine, from among the at least one ultrasound still cut corresponding to the first time stamp, at least one second output image including ECG information that is closest to the first ECG information. An operation of the ultrasound diagnosis apparatus 1000 determining a second output image will be described in more detail below with reference to FIG. 9B.

The ultrasound diagnosis apparatus 1000 may transmit the at least one second output image to the client apparatus 200 (S820).

According to embodiments, by determining a second output image based on the first time stamp and the first ECG information received from the client apparatus 200, the ultrasound diagnosis apparatus 1000 may provide the client apparatus 200 with an ultrasound still cut that is relatively close to a still cut requested by the client apparatus 200.

Furthermore, in a cardiac ultrasound scan, information that can be observed may vary according to an ECG cycle. For acquisition of an ultrasound image of the heart, an ECG cycle at a time point when the ultrasound image is acquired may be an important factor to consider when making a diagnosis. According to embodiments, the ultrasound diagnosis apparatus 1000 may determine an ultrasound still cut to be provided to the client apparatus 200 based on ECG information as well as a time stamp corresponding to a time point when a still cut is requested. Thus, the ultrasound diagnosis apparatus 1000 may provide an ultrasound still cut that better matches the intent of the user of the client apparatus 200.

Figure 9A:
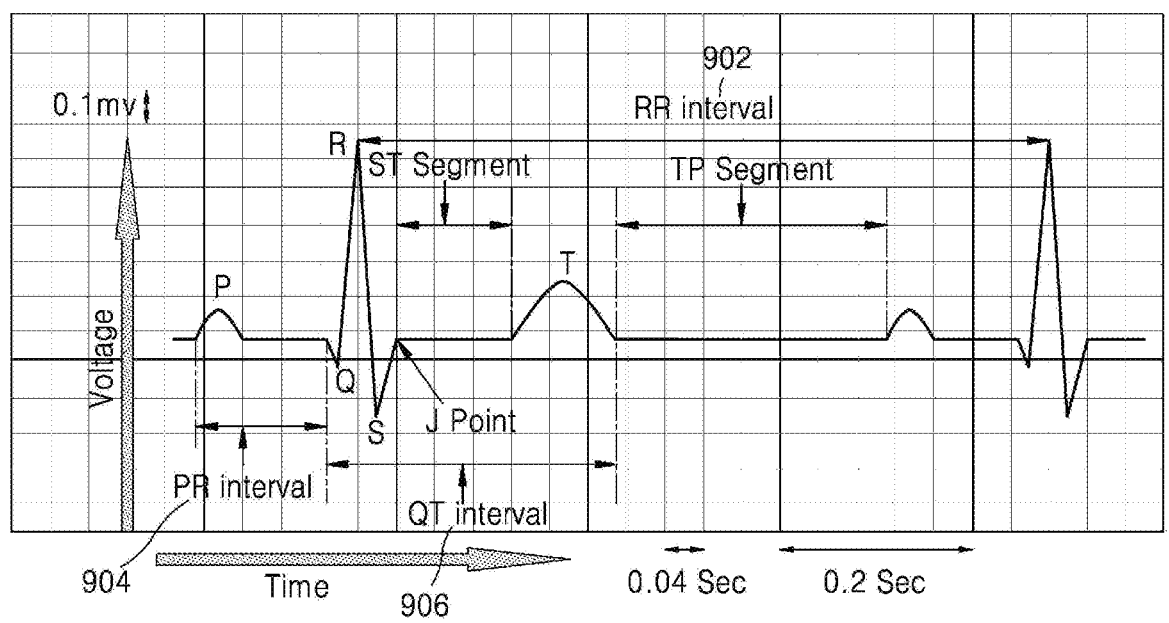
FIGS. 9A and 9B are diagrams for explaining an operation of an ultrasound diagnosis apparatus determining at least one output image based on a time stamp and ECG data, according to an embodiment.
Figure 9B:
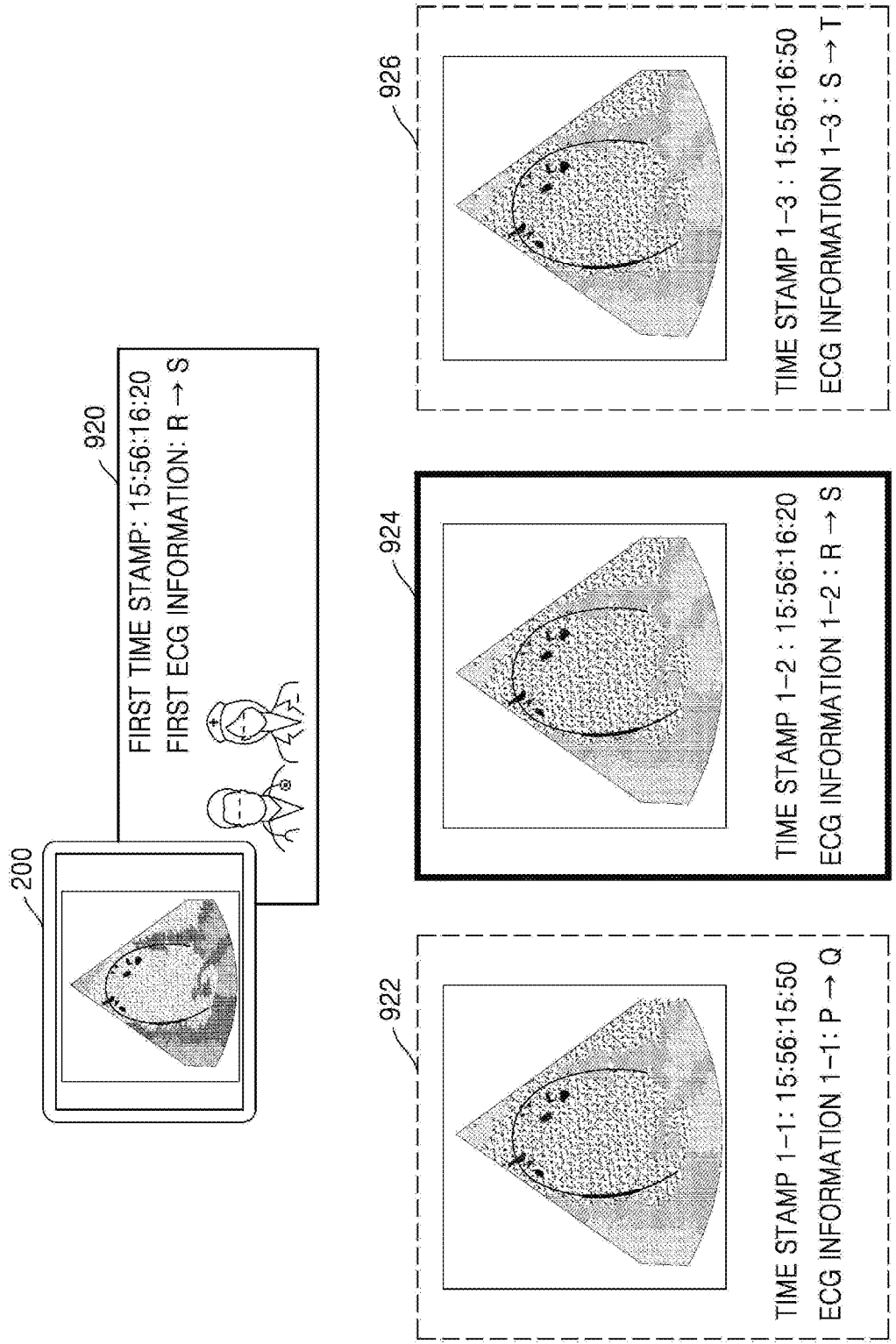

FIGS. 9A and 9B are diagrams for explaining an operation of the ultrasound diagnosis apparatus (1000 of FIG. 3) determining at least one output image based on a time stamp and ECG data, according to an embodiment.

ECG is a graphical recording of electrical activity generated during each heartbeat by inducing weak electrical signals from a predetermined portion of a body surface and amplifying the weak electrical signals. Furthermore, a test performed to acquire an ECG is referred to as electrocardiography. In the present specification, ECG data may be data acquired by performing electrocardiography.

FIG. 9A illustrate ECG data according to an embodiment. The ECG data may be expressed as an electrical potential (mV) with respect to time (sec). Furthermore, for example, the ECG data may include P, Q, R, S, and T waves. Types of the waves included in the ECG data are not limited thereto, and the ECG data may include more or fewer types of waves depending on the accuracy and type of electrocardiography.

Furthermore, the ECG data may show a repeated pattern of predetermined types of waves corresponding to a cardiac cycle. For example, when the heart is in a stable state, one heartbeat may occur over a period of 0.6 sec to 1.0 sec. Thus, waves included in the ECG data may have a time interval of 0.6 sec to 1.0 sec.

Referring to FIG. 9A, RR interval 902 that is a time interval between two adjacent R waves may be 0.6 sec to 1.0 sec. Furthermore, PR interval 904 that is a time interval between P and R waves may be 0.12 sec to 0.20 sec. QT interval 906 that is a time interval between Q and T waves may be 0.12 sec to 0.20 sec. In this way, since an ECG cycle repeats over a relatively short period, the ultrasound diagnosis apparatus 1000 may additionally use ECG information to provide an ultrasound still cut that matches a still cut requested by a user of the client apparatus 200.

FIG. 9B is a diagram for explaining an operation of the ultrasound diagnosis apparatus 1000 determining a second output image based on first ECG information from among at least one ultrasound still cut 922, 924, and 926 corresponding to a first time stamp, according to an embodiment.

For example, the ultrasound diagnosis apparatus 1000 may receive a request 920 for a still cut including a first time stamp '15:56:16:20' and first ECG information 'R→S' from the client apparatus 200. In this case, the ultrasound diagnosis apparatus 1000 may determine the at least one ultrasound still cut 922, 924, and 926 corresponding to the first time stamp, from among at least one ultrasound still cut stored in the memory 1030 together with their corresponding time stamps and ECG information. Since the embodiments described with respect to FIG. 5 may be applied to the operation of the ultrasound diagnosis apparatus 1000 determining at least one ultrasound still cut corresponding to the first time stamp, a detailed description thereof will be omitted herein.

In an embodiment, the ultrasound diagnosis apparatus 1000 may determine at least one second output image corresponding to the first ECG information, based on pieces of ECG information respectively included in the at least one ultrasound still cut 922, 924, and 926 corresponding to the first time stamp. The ultrasound diagnosis apparatus 1000 may determine an ultrasound still cut including ECG information close to the first ECG information as a second output image. For example, the at least one ultrasound still cut 922, 924, and 926 corresponding to the first time stamp may include an ultrasound still cut 1-1 922, an ultrasound still cut 1-2 924, and an ultrasound still cut 1-3 926. Furthermore, the ultrasound still cut 1-1 922 through the ultrasound still cut 1-3 926 may respectively include ECG information 1-1 'P-Q', ECG information 1-2 'R→S', and ECG information 1-3 'S→T'. In this case, the ultrasound diagnosis apparatus 1000 may determine as the second output image the ultrasound still cut 1-2 924 including the ECG information 1-2 'R→S' that corresponds to the first ECG information 'R→S' included in the request 920 received from client apparatus 200.

Although it has been described that the ECG information 'R→S' regarding the ultrasound still cut 1-2 924 corresponds to the first ECG information 'R→S', embodiments are not limited thereto. The ultrasound diagnosis apparatus 1000 may determine, based on a time interval between waves included in ECG data, a second output image including ECG information closest to the first ECG information from among the at least one ultrasound still cut 922, 924, and 926 corresponding to the first time stamp.

According to embodiments, by additionally using ECG information in determining an ultrasound still cut to be provided to the client apparatus 200, the ultrasound diagnosis apparatus 1000 may determine an ultrasound still cut that better matches the request 920 made by the client apparatus 200 for a still cut.

FIG. 10 is a flowchart of a method FIG. 10 is a flowchart of a method, performed by an ultrasound diagnosis apparatus 1000, of transmitting an ultrasound image and a time stamp to a client apparatus 200, according to an embodiment.

Referring to FIG. 10, the ultrasound diagnosis apparatus 1000 may store, in the memory (1030 of FIG. 3), at least one obtained ultrasound still cut at respective first time intervals, together with their corresponding time stamps (S1010-2). Since the embodiments described with respect to operation S610-2 in FIG. 6 may be applied to operation S1010-2, a detailed description thereof will be omitted herein.

The ultrasound diagnosis apparatus 1000 may transmit an ultrasound image and a time stamp to the client apparatus 200 (S1010-4). Operation S1010-4 may be performed simultaneously with operation S1010-2 described above. Furthermore, since embodiments described with respect to operation S610-4 in FIG. 6 may be applied to operation S1010-4, a detailed description thereof will be omitted herein.

The client apparatus 200 may display the received ultrasound image in real-time (S1012). Since the embodiments described with respect to operation S612 in FIG. 6 may be applied to operation S1012, a detailed description thereof will be omitted herein.

The ultrasound diagnosis apparatus 1000 may receive a first input for stopping transmission of an ultrasound image to the client apparatus 200 (S1014).

According to an embodiment, the ultrasound diagnosis apparatus 1000 may receive, during acquisition of an ultrasound image of an object, a first input for stopping transmission of the ultrasound image to the client apparatus 200 from a user (e.g., a sonographer) via a user interface (not shown).

Since diagnosis information of a patient is personal information, even a doctor may not receive all types of diagnosis information of the patient. For example, a sonographer may transmit an ultrasound image in real-time to a doctor at a remote location in a streaming manner while capturing an ultrasound image of a patient. However, while the sonographer captures an ultrasound image of a body part that should not be shared with the doctor, it is necessary to stop transmission of the ultrasound image to the client apparatus 200.

The ultrasound diagnosis apparatus 1000 may stop transmission of the ultrasound image based on the first input and transmit only a time stamp corresponding to the acquired ultrasound image to the client apparatus 200 (S1016).

According to an embodiment, even when transmission of the ultrasound image to the client apparatus 200 is stopped, the ultrasound diagnosis apparatus 1000 may continuously transmit its corresponding time stamp. By doing so, when transmission of an ultrasound image to the client apparatus 200 is subsequently resumed, the ultrasound diagnosis apparatus 1000 may keep a time stamp corresponding to at least one ultrasound still cut stored in the memory 1030 in sync with a time stamp being transmitted to the client apparatus 200.

The ultrasound diagnosis apparatus 1000 may receive a second input for resuming transmission of an ultrasound image to the client apparatus 200 (S1018).

In an embodiment, the ultrasound diagnosis apparatus 1000 may receive a second input for controlling resumption of transmission of an ultrasound image to the client apparatus 200 from the user via the user interface.

The ultrasound diagnosis apparatus 1000 may transmit to the client apparatus 200 an obtained ultrasound image and a time stamp indicating a time when the ultrasound image is obtained (S1020).

Since the embodiments described with respect to operation S1010-4 may be applied to the operation of transmitting the obtained ultrasound image and its corresponding time stamp to the client apparatus 200, a detailed description thereof will be omitted herein.

The client apparatus 200 may display the ultrasound image received from the ultrasound diagnosis apparatus 1000 in real-time on a display (S1022). Since the embodiments described with respect to operation S1012 may be applied to operation S1022, a detailed description thereof will be omitted herein.

Figure 11:
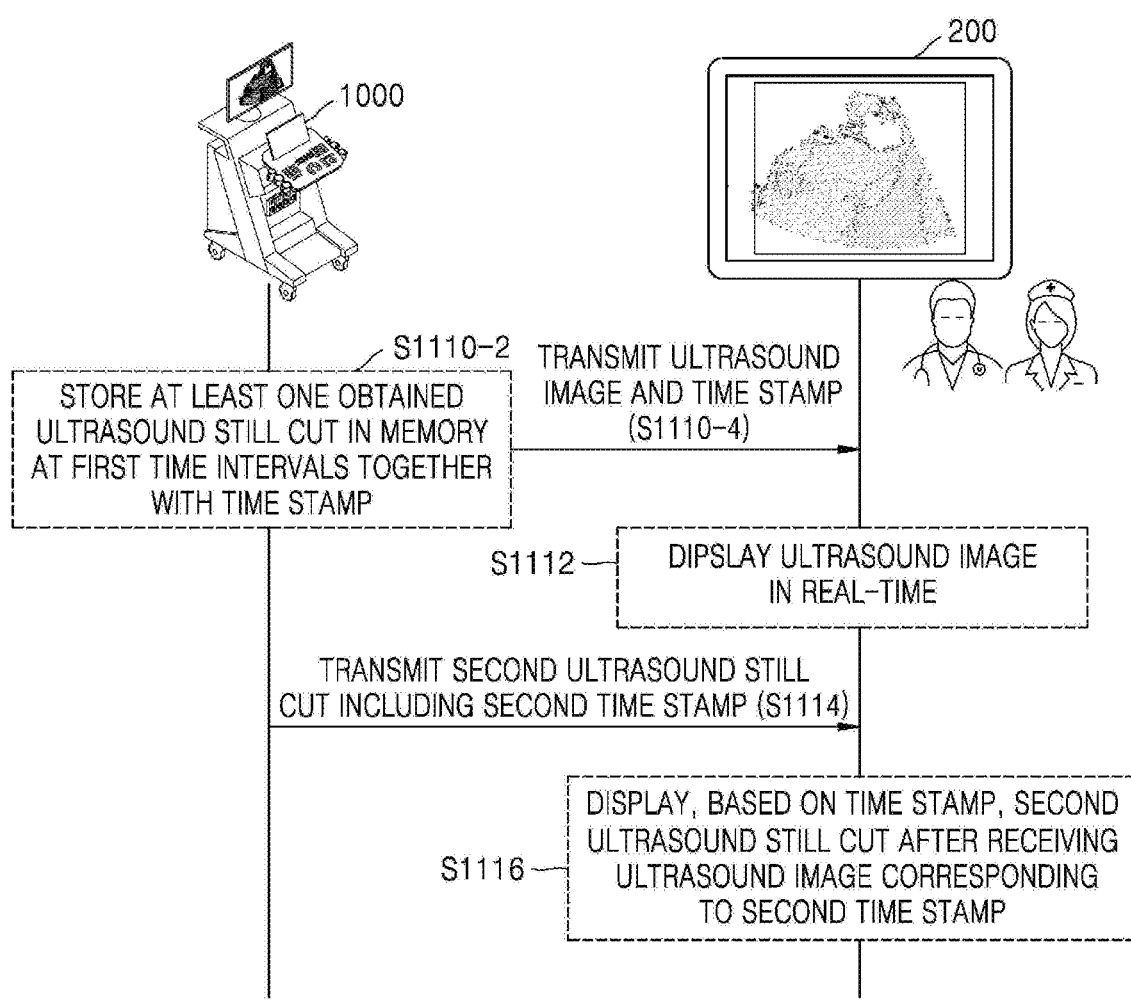
FIG. 11 is a flowchart of a method, performed by an ultrasound diagnosis apparatus, of transmitting an ultrasound still cut to a client apparatus, according to an embodiment.

FIG. 11 is a flowchart of a method, performed by an ultrasound diagnosis apparatus 1000, of transmitting an ultrasound still cut to a client apparatus 200, according to an embodiment.

Referring to FIG. 11, the ultrasound diagnosis apparatus 1000 may store at least one obtained ultrasound still cut in the memory (1030 of FIG. 3) at respective first time intervals, together with their corresponding time stamps (S1110-2). Since the embodiments described with respect to operation S610-2 in FIG. 6 may be applied to operation S1110-2, a detailed description thereof will be omitted herein.

The ultrasound diagnosis apparatus 1000 may transmit to the client apparatus 200 an obtained ultrasound image and a time stamp indicating a time when the ultrasound image is obtained (S1110-4). Operation S1110-4 may be performed simultaneously with operation S1110-2. Furthermore, since embodiments described with respect to operation S610-4 in FIG. 6 may be applied to operation S1110-4, a detailed description thereof will be omitted herein.

The ultrasound diagnosis apparatus 1000 may transmit a second ultrasound still cut including a second time stamp to the client apparatus 200 (S1114).

A skilled sonographer may provide the client apparatus 200 with an ultrasound still cut with respect to an ultrasound image, which is determined to be necessary for diagnosis of a patient during ultrasound imaging performed by the ultrasound diagnosis apparatus 1000, before a doctor at a remote location requests the ultrasound still cut from him or her. Thus, according to an embodiment, during ultrasound imaging, the ultrasound diagnosis apparatus 1000 may receive via a user interface an input for transmitting a second ultrasound still cut acquired at a particular time point and its corresponding second time stamp to the client apparatus 200.

The client apparatus 200 may display the second ultrasound still cut after receiving an ultrasound image corresponding to the second time stamp, based on a time stamp received in real-time from the ultrasound diagnosis apparatus 1000 (S1116).

Data may be transmitted at different speeds depending on a network environment or a size of data to be transmitted. For example, the second ultrasound still cut may be transmitted at a higher speed than an ultrasound image transmitted in real-time to the client apparatus 200 in a streaming manner. In this case, the second ultrasound still cut with respect to the ultrasound image corresponding to the second time stamp may be received by the client apparatus 200 faster than the ultrasound image corresponding to the second time stamp. Thus, according to an embodiment, the client apparatus 200 may control a display to display, based on a time stamp being received by the ultrasound diagnosis apparatus 1000, the second ultrasound still cut after receiving the ultrasound image corresponding to the second time stamp.

Figure 12:
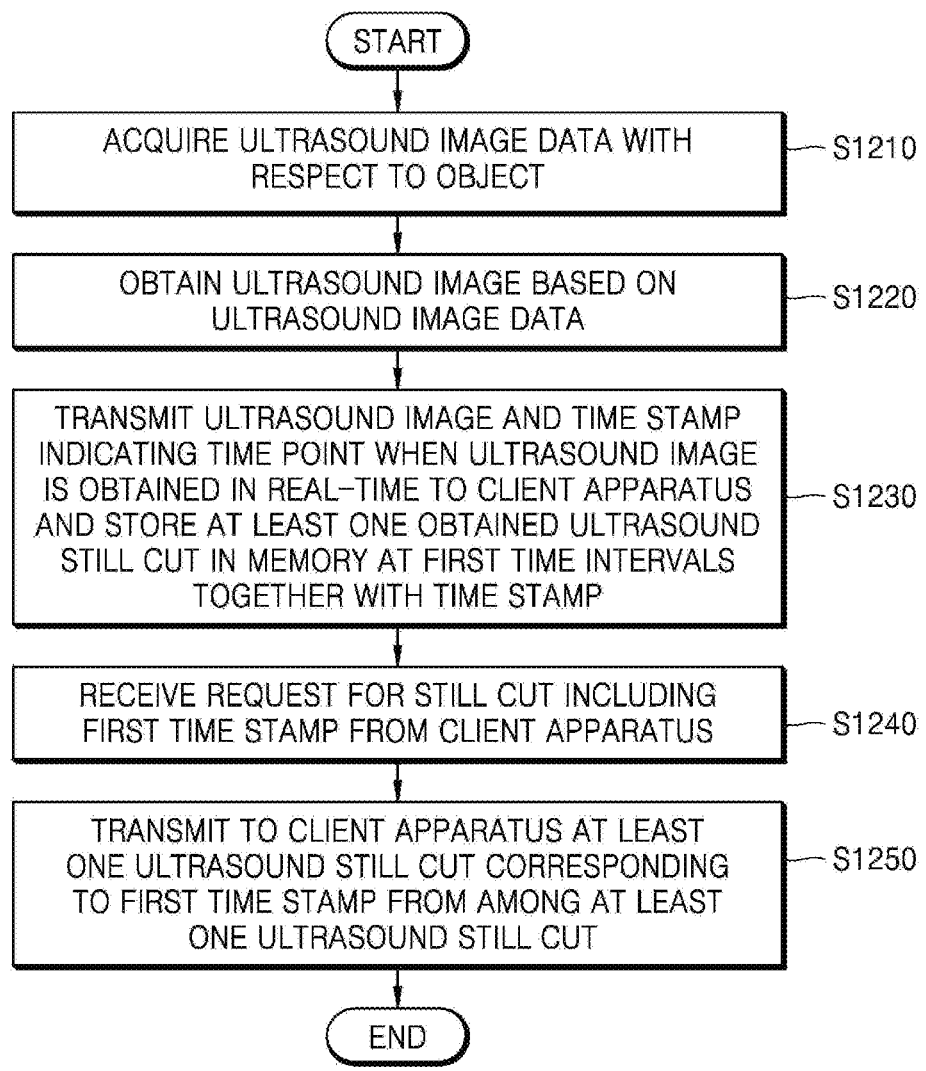
FIG. 12 is a flowchart of a method, performed by an ultrasound diagnosis apparatus, of transmitting at least one ultrasound still cut to a client apparatus, according to an embodiment.

FIG. 12 is a flowchart of a method, performed by the ultrasound diagnosis apparatus 1000, of transmitting at least one ultrasound still cut to the client apparatus 200, according to an embodiment.

The method of transmitting at least one ultrasound still cut may be performed by the ultrasound diagnosis apparatus 1000 having the above-described configuration.

Referring to FIG. 12, the ultrasound diagnosis apparatus 1000 may acquire ultrasound image data with respect to an object (S1210).

The ultrasound diagnosis apparatus 1000 may obtain an ultrasound image based on the ultrasound image data (S1220).

According to an embodiment, the ultrasound diagnosis apparatus 1000 may transmit ultrasound signals to the object and then receive ultrasound echo signals reflected from the object. Furthermore, the ultrasound diagnosis apparatus 1000 may acquire ultrasound image data with respect to the object based on the received ultrasound echo signals.

The ultrasound diagnosis apparatus 1000 may transmit the ultrasound image and a time stamp indicating a time when the ultrasound image is obtained in real-time to the client apparatus 200 and store at least one obtained ultrasound still cut in the memory 1030 at respective first time intervals, together with their corresponding time stamps (S1230).

In an embodiment, the ultrasound diagnosis apparatus 1000 may obtain an ultrasound image by processing in real-time ultrasound image data acquired by scanning the object. The ultrasound image obtained in real-time by the ultrasound diagnosis apparatus 1000 may be a still image or moving image.

Furthermore, the ultrasound diagnosis apparatus 1000 may transmit the ultrasound image and a time stamp indicating a time when the ultrasound image is obtained in real-time to the client apparatus 200. According to an embodiment, when the ultrasound image obtained by the ultrasound diagnosis apparatus 1000 is a moving image, the ultrasound diagnosis apparatus 1000 may transmit the ultrasound image in such a manner as to be streamed to the client apparatus 200 in real-time. Furthermore, the ultrasound diagnosis apparatus 1000 may transmit a continuous time stamp corresponding to the ultrasound image being streamed to the client apparatus 200.

According to an embodiment, the ultrasound diagnosis apparatus 1000 may process the obtained ultrasound image and transmit the resulting ultrasound image in real-time to the client apparatus 200. For example, processing performed on the ultrasound image by the ultrasound diagnosis apparatus 1000 may include transcoding. The ultrasound diagnosis apparatus 1000 may perform the processing to convert the obtained ultrasound image into an ultrasound image with a lower resolution than an original image and transmit the resulting image to the client apparatus 200. In another embodiment, the ultrasound diagnosis apparatus 1000 may provide the obtained ultrasound image to an external server and obtain a processed ultrasound image from the external server. By performing the processing, it is possible to reduce a size of an ultrasound image being transmitted to the client apparatus 200, thereby accommodating a limited network bandwidth.

Furthermore, the ultrasound diagnosis apparatus 1000 may store at least one obtained ultrasound still cut in the memory 1030 at respective first time intervals, together with their corresponding time stamps. For example, the ultrasound diagnosis apparatus 1000 may store an ultrasound still cut with respect to an ultrasound image obtained in real-time every first time interval. Furthermore, the ultrasound diagnosis apparatus 1000 may store a time stamp corresponding to an ultrasound still cut every first time interval, together with the ultrasound still cut.

The ultrasound diagnosis apparatus 1000 may receive a request for a still cut including a first time stamp from the client apparatus 200 (S1240).

According to an embodiment, the ultrasound diagnosis apparatus 1000 may receive a request for a still cut including a first time stamp from the client apparatus 200 via the communicator 1040.

The ultrasound diagnosis apparatus 1000 may transmit to the client apparatus 200 at least one ultrasound still cut corresponding to the first time stamp from among the at least one ultrasound still cut (S1250).

According to an embodiment, the ultrasound diagnosis apparatus 1000 may determine, according to the request made by the client apparatus 200 for a still cut, at least one ultrasound still cut corresponding to the first time stamp from among the at least one ultrasound still cut stored in the memory 1030. The ultrasound diagnosis apparatus 1000 may determine, based on the time stamps stored in the memory 1030 together with the at least one ultrasound still cut, at least one ultrasound still cut corresponding to the first time stamp from among the stored at least one ultrasound still cut.

Furthermore, the ultrasound diagnosis apparatus 1000 may transmit the at least one ultrasound still cut corresponding to the first time stamp to the client apparatus 200. The processor 1020 may control the communicator 1040 to transmit the determined at least one ultrasound still cut corresponding to the first time stamp to the client apparatus 200.

According to embodiments, by transmitting an ultrasound still cut image based on a time stamp, the ultrasound diagnosis apparatus 1000 may provide an ultrasound still cut that is close to a still cut requested by the client apparatus 200 despite the presence of a network delay time.

Furthermore, embodiments may be implemented as a software program including instructions stored in computer-readable storage media.

A computer is a device capable of calling stored instructions from storage media and performing operations in embodiments according to the called instructions and may include an ultrasound diagnosis apparatus according to embodiments.

The computer-readable storage media may be provided in the form of non-transitory storage media. The term 'non-transitory' only means that the storage media do not include signals and are tangible media, and does not distinguish whether data is semi-permanently or temporarily stored on the storage media.

In addition, ultrasound diagnosis apparatuses or methods according to embodiments may be included in a computer program product when provided. The computer program product may be traded as a commodity between a seller and a buyer.

The computer program product may include a software program and a computer-readable storage medium having the software program stored thereon. For example, the computer program product may include goods (e.g., downloadable apps) in the form of a software program electronically distributed via a manufacturer of an ultrasound diagnosis apparatus or an electronic market (e.g., Google Play Store and App Store). For electronic distribution, at least some software programs may be stored in storage media or may be created temporarily. In this case, the storage media may be storage media contained in a manufacturer's server, a server of an electronic market, or a relay server for temporarily storing a software program.

The computer program product may include a storage medium of a server or a terminal in a system composed of the server and the terminal (e.g., an ultrasound diagnosis apparatus). When a third device (e. g., a smartphone) is connected to a server or terminal through a communication network, the computer program product may include a storage medium of the third device. Furthermore, the computer program product may include a software program itself that is transmitted from a server to a terminal or a third device or from the third device to the terminal.

In this case, one of the server, the terminal, and the third device may run the computer program product to perform methods according to embodiments. Alternatively, two or more of the server, the terminal, and the third device may run the computer program product to implement methods according to embodiments in a distributed manner.

For example, a server (e.g., a cloud server or an artificial intelligence (AI) server) may run a computer program product stored thereon to control a terminal connected to the server through a communication network to perform methods according to embodiments.

As another example, a third device may run a computer program product to control a terminal connected to the third device through a communication network to perform methods according to embodiments. In detail, the third device may remotely control an ultrasound diagnosis apparatus to transmit ultrasound signals to an object and generate an image of an inner area of the object based on information about signals reflected from the object.

As another example, a third device may run a computer program product to directly perform methods according to embodiments based on a value input from an auxiliary device (e.g., a probe for medical equipment). In detail, the auxiliary device may transmit ultrasound signals to an object and acquire ultrasound signals reflected from the object. The third device may receive information about the reflected ultrasound signals from the auxiliary device and generate an image of an inner part of the object based on the received information.

When a third device runs a computer program product, the third device may download the computer program product from a server and execute the downloaded computer program product. Alternatively, the third device may run a preloaded computer program product to perform methods according to embodiments.

What is claimed is:

1. An ultrasound diagnosis apparatus comprising:
a probe configured to acquire ultrasound image data with respect to an object by transmitting ultrasound signals to the object,
one or more processors configured to obtain an ultrasound image based on the ultrasound image data, transmit the ultrasound image and a time stamp indicating a time point when the ultrasound image is obtained in real-time to a client apparatus, and store, in a memory, at least one obtained ultrasound still cut by selecting the ultrasound image as the at least one obtained ultrasound still cut at respective first time intervals, together with the time stamp; and
a communicator configured to receive a request for a still cut including a first time stamp from the client apparatus,
wherein the one or more processors are further configured to transmit to the client apparatus at least one ultrasound still cut corresponding to the first time stamp from among the stored at least one obtained ultrasound still cut.

2. The ultrasound diagnosis apparatus of claim 1, wherein the one or more processors are further configured to convert the ultrasound image into an ultrasound image with a lower resolution than an original version, to obtain a resulting ultrasound image, and transmit the resulting ultrasound image and the time stamp to the client apparatus, and
wherein the at least one ultrasound still cut is the original version of the ultrasound image.

3. The ultrasound diagnosis apparatus of claim 1, wherein the one or more processors are further configured to determine the respective first time intervals based on a network delay time between the ultrasound diagnosis apparatus and the client apparatus.

4. The ultrasound diagnosis apparatus of claim 3, wherein the one or more processors are further configured to determine the respective first time intervals when the at least one ultrasound still cut that corresponds to the time stamp and is obtained during a time between a current time point and a time point that is the network delay time before the current time point is stored in the memory.

5. The ultrasound diagnosis apparatus of claim 1, wherein the one or more processors are further configured to transmit at least one ultrasound still cut including a time stamp corresponding to a time point closest to the first time stamp from among the stored at least one ultrasound still cut.

6. The ultrasound diagnosis apparatus of claim 1, wherein the communicator is further configured to receive a first captured image acquired by the client apparatus at a time point corresponding to the first time stamp.

7. The ultrasound diagnosis apparatus of claim 6, wherein the one or more processors are further configured to determine, based on a degree of similarity between each of the at least one ultrasound still cut corresponding to the first time stamp and the first captured image, at least one first output image with the degree of similarity that is greater than or equal to a predetermined threshold from among the at least one ultrasound still cut corresponding to the first time stamp and to transmit the at least one first output image to the client apparatus.

8. The ultrasound diagnosis apparatus of claim 6, wherein the one or more processors are further configured to determine, based on a degree of similarity between each of the at least one ultrasound still cut corresponding to the first time stamp and the first captured image, at least one second output image with a highest degree of similarity from among the at least one ultrasound still cut corresponding to the first time stamp and to transmit the at least one second output image to the client apparatus.

9. The ultrasound diagnosis apparatus of claim 1, further comprising an input interface further configured to receive a first input of stopping transmission of the ultrasound image to the client apparatus,
wherein the one or more processors are further configured to stop transmission of the ultrasound image to the client apparatus based on the first input and transmit only the time stamp to the client apparatus.

10. A method of controlling an ultrasound diagnosis apparatus, the method comprising:
acquiring ultrasound image data with respect to an object by transmitting ultrasound signals to the object;
obtaining an ultrasound image based on the ultrasound image data,
transmitting the ultrasound image and a time stamp indicating a time point when the ultrasound image is obtained in real-time to a client apparatus and storing, in a memory, at least one obtained ultrasound still cut by selecting the ultrasound image as the at least one obtained ultrasound still cut at respective first time intervals, together with the time stamp;
receiving a request for a still cut including a first time stamp from the client apparatus; and
transmitting to the client apparatus at least one ultrasound still cut corresponding to the first time stamp from among the stored at least one obtained ultrasound still cut.

11. The method of claim 10, wherein the transmitting of the ultrasound image and the time stamp indicating the time point when the ultrasound image is obtained in real-time to the client apparatus comprises:
converting the ultrasound image into an ultrasound image with a lower resolution than an original version, to obtain a resulting ultrasound image; and
transmitting the resulting ultrasound image and the time stamp to the client apparatus, and
wherein the at least one ultrasound still cutis the original version of the ultrasound image.

12. The method of claim 10, wherein the storing of the at least one obtained ultrasound still cut, in the memory at the respective first time intervals together with the time stamp comprises determining the respective first time intervals based on a network delay time between the ultrasound diagnosis apparatus and the client apparatus.

13. The method of claim 12, wherein the determining of the respective first time intervals comprises determining the respective first time intervals when the at least one ultrasound still cut that corresponds to the time stamp and is obtained during a time between a current time point and a time point that is the network delay time before the current time point is stored in the memory.

14. The method of claim 10, wherein the transmitting of the at least one ultrasound still cut corresponding to the first time stamp to the client apparatus comprises transmitting at least one ultrasound still cut including a time stamp corresponding to a time point closest to the first time stamp from among the stored at least one ultrasound still cut.

15. The method of claim 10, wherein the receiving of the request for the still cut including the first time stamp from the client apparatus comprises receiving a first captured image acquired by the client apparatus at a time point corresponding to the first time stamp.

16. The method of claim 15, wherein the transmitting of the at least one ultrasound still cut corresponding to the first time stamp to the client apparatus comprises:
- determining, based on a degree of similarity between each of the at least one ultrasound still cut corresponding to the first time stamp and the first captured image, at least one first output image with the degree of similarity that is greater than or equal to a predetermined threshold from among the at least one ultrasound still cut corresponding to the first time stamp; and
- transmitting the at least one first output image to the client apparatus.

17. The method of claim 15, wherein the transmitting of the at least one ultrasound still cut corresponding to the first time stamp to the client apparatus comprises:
- determining, based on a degree of similarity between each of the at least one ultrasound still cut corresponding to the first time stamp and the first captured image, at least one second output image with a highest degree of similarity from among the at least one ultrasound still cut corresponding to the first time stamp; and
- transmitting the at least one second output image to the client apparatus.

18. The method of claim 10, further comprising receiving a first input of stopping transmission of the ultrasound image to the client apparatus,
- wherein the transmitting of the ultrasound image and the time stamp indicating the time point when the ultrasound image is obtained in real-time to the client apparatus comprises stopping transmission of the ultrasound image to the client apparatus based on the first input and transmitting only the time stamp to the client apparatus.

19. A computer program product comprising a non-transitory computer-readable recording medium having recorded thereon a program for performing the method of claim 10 on a computer.

* * * * *